(12) United States Patent
Vogelstein et al.

(10) Patent No.: US 11,268,153 B2
(45) Date of Patent: Mar. 8, 2022

(54) HEAD AND NECK SQUAMOUS CELL CARCINOMA ASSAYS

(71) Applicant: The Johns Hopkins University, Baltimore, MD (US)

(72) Inventors: Bert Vogelstein, Baltimore, MD (US); Kenneth W. Kinzler, Baltimore, MD (US); Luis Diaz, Ellicot City, MD (US); Nickolas Papadopoulos, Towson, MD (US); Nishant Agrawal, Baltimore, MD (US); Yuxuan Wang, Baltimore, MD (US); Simeon Springer, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 331 days.

(21) Appl. No.: 15/739,610

(22) PCT Filed: Jun. 16, 2016

(86) PCT No.: PCT/US2016/037793
§ 371 (c)(1),
(2) Date: Dec. 22, 2017

(87) PCT Pub. No.: WO2016/209703
PCT Pub. Date: Dec. 29, 2016

(65) Prior Publication Data
US 2018/0171413 A1   Jun. 21, 2018

Related U.S. Application Data
(60) Provisional application No. 62/182,757, filed on Jun. 22, 2015.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/156* (2013.01); *C12Q 2600/158* (2013.01)

(58) Field of Classification Search
CPC .................................................. C12Q 1/6886
See application file for complete search history.

(56) References Cited

U.S. PATENT DOCUMENTS

2014/0329230 A1   11/2014   Franzmann et al.

OTHER PUBLICATIONS

Gasco, M. et al. Oral Oncology 39:222-231. (Year: 2003).*
(Continued)

*Primary Examiner* — Diana B Johannsen
(74) *Attorney, Agent, or Firm* — Fish & Richardson P.C.

(57) ABSTRACT

We queried DNA from saliva or plasma of 93 HNSCC patients, searching for somatic mutations or human papillomavirus genes, collectively referred to as tumor DNA. When both plasma and saliva were tested, tumor DNA was detected in 96% (95% CI, 84% to 99%) of 47 patients. The fractions of patients with detectable tumor DNA in early- and late-stage disease were 100% (n=10) and 95% (n=37), respectively. Saliva is preferentially enriched for tumor DNA from the oral cavity, whereas plasma is preferentially enriched for tumor DNA from the other sites. Tumor DNA in the saliva and plasma is a valuable biomarker for detection of HNSCC.

19 Claims, 29 Drawing Sheets

Specification includes a Sequence Listing.

(56) References Cited

OTHER PUBLICATIONS

Feldman, R. et al. Journal of Clinical Oncology 32(15 suppl):680 (May 20, 2014). (Year: 2014).*
Agrawal et al., "Comparative Genomic Analysis of Esophageal Adenocarcinoma and Squamous Cell Carcinoma", Cancer discovery 2, 899-905 (2012).
Agrawal et al., "Exome Sequencing of Head and Neck Squamous Cell Carcinoma Reveals Inactivating Mutations in NOTCH1", Science, 333(6046): 1154-1157, 2011.
Ahn et al., "Saliva and plasma quantitative polymerase chain reaction-based detection and surveillance of human papillomavirus—related head and neck cancer," JAMA Otolaryngology—Head & Neck Surgery, vol. 140, No. 9, pp. 846-854 (Jul. 31, 2014) Abstract.
Allison et al., "The role of professional diagnosis delays is the prognosis of upper aerodigestivetract carcinoma", Oral oncology 34, 147-153 (1998).
Bettegowda et al., "Detection of circulating tumor DNA in early- and late-stage human malignancies" Science Translational Medicine, vol. 6, Issue 224, Article No. 224ra24, Internal pp. 1-14 (Feb. 19, 2014).
Bettegowda et al., "Mutations in CIC and FUBP1 contribute to human oligodendroglioma", Science 333, 1453-1455 (2011).
Boyle et al., "Gene mutations in saliva as molecular markers for head and neck squamous cell carcinomas", American journal of surgery 168, 429-432 (1994).
Cancer Genome Atlas, Comprehensive genomic characterization of head and neck squamous cell carcinomas. Nature 517, 576-582 (2015).
Carvalho et al., "Predictive factors for diagnosis of advanced-stage squamous cell carcinoma of the head and neck", Archives of otolaryngology—head & neck surgery 128, 313-318 (2002).
Chaturvedi et al., "Human papillomavirus and rising oropharyngeal cancer incidence in the United States", Journal of clinical oncology: official journal of the American Society Clinical Oncology 29, 4294-4301 (2011).
Chaturvedi et al., "Incidence trends for human papillomavirus-related and -unrelated oral squamous cell carcinomas in the United States", Journal clinical oncology: official journal of the American Society of Clinical Oncology 26, 612-619 (2008).
Chaturvedi et al., "Worldwide trends in incidence rates for oral cavity and oropharyngeal cancers". Journal of clinical oncology: official journal of the American Society of Clinical Oncology 31, 4550-4559 (2013).
Dawson et al., "Analysis of circulating tumor DNA to monitor metastatic breast cancer", The New England journal of medicine, 368, pp. 1199-1209 (2013).
Diehl et al., "Analysis of mutations m DNA isolated from plasma and stool of colorectal cancer patients", Gastroenterology 135, 489-498 (2008).
D'Souza et al., "Case-control study of human papillomavirus and oropharyngeal cancer", The New England journal of medicine 356, 1944-1956 (2007).
Ewing et al., "Base-calling of automated sequencer traces using pherd. 1. Accuracy assessment", Genome Res. 8, 175-185 (1998).
Ferlay et al., Estimates of worldwide burden of cancer in 2008: GLOBOCAN 2008. International journal of cancer. Journal international du cancer 127, 2893-2917 (2010).
Gillison et al., "Prevalence of oral HPV infection in the United States", 2009-2010, Jama 307, 693-703 (2012).
Gourin et al., "Carcinoma of the hypopharynx", Surg. Oncol. Clin. N. Am. 13, 81-98 (2004).
Guggenheimer et al., "Factors delaying the diagnosis of oral and oropharyngeal carcinomas", Cancer 64, 932-935, (1989).
Hubers et al., "Molecular sputum analysis for the diagnosis of lung cancer", British journal of cancer 109, 530-537 (2013).
International Preliminary Report on Patentability issued in International Application No. PCT/US2016/037793, dated Jan. 4, 2018.
International Search Report and Written Opinion issued in International Application No. PCT/IS2016/037793, dated Sep. 20, 2016, 14 pages.
Isayeva et al., "Human papillomavirus in non-oropharyngeal head and neck cancers: a systematic literature review", Head and neck pathology 6, suppl. 1, S104-120 (2012).
Kang et al., "Emerging biomarkers in head and neck cancer in the era of genomics", Nat. Rev. Clin. Oncol., 12, 11-26, (2015).
Kinde et al., "Detection and qualification of rare mutations with massively parallel sequencing", Proceedings of the National Academy of Sciences of the United States of America 108, 9530-9535 (2012).
Kinde et al., "Evaluation of DNA from the Papanicolaou test to detect ovarian and endometrial cancer", Science translational medicine, 5, 167ra164 (2013).
Koivunen et al., "The impact of patient and professional diagnostic delays on survival in pharyngeal cancer", Cancer 92, 2885-2891 (2001).
Kowalski et al., "Influence of time delay and clinical upstaging in the prognosis of head and neck cancer", Oral oncology 37, 94-98 (2001).
Kreimer et al., "Human papillomavirus types in head and neck squamous cell carcinomas worldwide: a systematic review", Cancer epidemiology, biomarkers & prevention: a publication of the American Association for Cancer Research, cosponsored by the American Society of Preventive Oncology 14, 467-475 (2005).
Kreimer et al., "Oral human papillomavirus in healthy individuals: a systematic review of the literature", Sexually transmitted diseases 37, 386-391 (2010).
Kuo et al., "Hypopharyngeal cancer incidence, treatment, and survival: temporal trends in the United States", The Laryngoscope 124, 2064-2069 (2014).
Leary et al., "Development of personalized tumor biomarkers using massively parallel sequencing", Science translational medicine 2, 20ra14 (2010).
Leemans et al., "The molecular biology of head and neck cancer", Nat. Rev. Cancer 11, 9-22 (2011).
Li et al., "Clinical, genomic, and metagenomic characterization of oral tongue squamous cell carcinoma in patients who do not smoke", Head & neck, (2015).
Lingen et al., "Low etiologic fraction for high-risk human papillomavirus in oral cavity squamous cell carcinomas", Oral oncology 49, 1-8 (2013).
Lutzky et al,, "Biomarkers for cancers of the head and neck" Clinical Medicine Insights: Ear, Nose and Throat, vol. 1, pp. 5-15 (2008).
Martignetti et al., "Personalized ovarian cancer disease surveillance and detection of candidate theraputic DNA target in circulating tumor DNA", Neoplasia (New York, N.Y.) 16, 97-103 (2014).
Newman et al., "An ultrasensitive method for quantitating circulating tumor DNA with Broad patient coverage", Nat. Med. 20, 548-554 (2014).
Patel et al., "Increasing incidence of oral tongue squamous cell carcinoma in young white women, age 18 to 44 years", Journal of clinical oncology : official journal of the American Society of Clinical Oncology 29, 1488-1494 (2011).
Pfister et al., "Clinical practice guidelines in oncology", J. Natl. Compr. Cane. Netw. 12, 1454-1487 (2014).
Ralla e al., "Nucleic acid-based biomarkers in body fluids of patients with urologic malignancies", Crit. Rev. Clin. Lab. Sci. 51, 200-231 (2014).
Sausen et al., "Integrated genomic analyses identify ARID1A and ARID1B alterations in the childhood cancer neuroblastoma", Nature genetics, 45, 12-17 (2013).
Sidransky et al., "Identification of p53 gene mutations in bladder cancers and urine samples", Science 252, 706-709 (1991).
Sidransky et al., "Identification of ras oncogene mutations m the stool of patients with curable colorectal tumors", Science 256, 102-105 (1992).
Sidransky, "Nucleic acid-based methods for the detection of cancer.", Science 278, 1054-1059 (1997).
Siegel, "Cancer statistics", CA Cancer J Clin, (2015).

(56) References Cited

OTHER PUBLICATIONS

Simard et al., "Cancers with increasing incidence trends in the United States: 1999 through 2008", CA Cancer J Clin, (2012).
Stransky et al., "The mutational landscape of head and neck squamous cell carcmoma", Science 333, 1157-1160 (2011).
Vogelstein et al., "Cancer genome landscapes", Science 339, 1546-1558 (2013).
Vogelstein et al., "Digital PCR", Proceedings of the National Academy of Sciences of the United States of America 96, 9236-9241 (1991).
Wang et al., "Detection of somatic mutations and HPV in the saliva and plasma of patients with head and neck squamous eel 1 carcinomas", Science Translational Medicine, vol. 7, Issue 293, Article No. 293ra104, Internal pp. 1-9 (Jun. 24, 2015) See pp. 3-5.
Wildt et al., "Delay in diagnosis of oral squamous cell carcinoma", Clin. Otolaryngol Allied Sci. 20, 21-25 (1995)

\* cited by examiner

Table S1: Patient Demographics

| Patient ID | Age at Diagnosis | Gender | Site | Subsite | Stage | T Classification | N Classification | Tumor HPV (by PCR) | Saliva Tumor DNA | Plasma Tumor DNA |
|---|---|---|---|---|---|---|---|---|---|---|
| HN 358 | 34 | M | OC | Tongue | III | T2 | N1 | - | + | - |
| HN 359 | 67 | M | L | Glottic | III | T3 | N0 | - | + | + |
| HN 361 | 68 | M | OC | Tongue | I | T1 | N0 | - | + | + |
| HN 362 | 56 | M | OP | Base of tongue | IV | T1 | N2 | + | - | NA |
| HN 363 | 61 | F | OC | Buccal mucosa | II | T2 | N0 | - | + | + |
| HN 364 | 61 | M | OC | Tongue | IV | T4 | N2 | - | + | + |
| HN 365 | 57 | M | OP | Soft palate | II | T2 | N0 | + | + | + |
| HN 366 | 70 | M | OC | Alveolar ridge | IV | T4a | N0 | - | + | + |
| HN 367 | 58 | M | OP | Base of tongue | IV | T2 | N2 | + | + | + |
| HN 368 | 50 | M | OC | Tongue | I | T1 | N0 | - | + | + |
| HN 369 | 74 | M | L | Supraglottic | II | T2 | N0 | - | + | NA |
| HN 370 | 54 | M | OC | Buccal mucosa | IV | T2 | N2 | - | + | + |
| HN 371 | 77 | F | OC | Tongue | I | T1 | N0 | - | + | NA |
| HN 372 | 61 | M | OP | Base of tongue | II | T2 | N0 | - | + | + |
| HN 373 | 69 | M | L | Supraglottic | III | T3 | N0 | - | - | + |
| HN 375 | 54 | M | OC | Alveolar ridge | I | T1 | N0 | - | + | NA |
| HN 377 | 55 | M | OP | Base of tongue | IV | T2 | N2 | + | - | + |
| HN 380 | 65 | M | L | Transglottic | IV | T4a | N0 | - | + | + |
| HN 381 | 45 | M | OC | Tongue | II | T2 | N0 | - | + | + |
| HN 382 | 48 | F | OC | Buccal mucosa | IV | T4a | N0 | - | + | NA |
| HN 383 | 61 | M | OC | Tongue | I | T1 | N0 | - | + | + |
| HN 384 | 68 | M | OP | Base of tongue | IV | T1 | N2 | + | - | + |
| HN 385 | 54 | F | L | Supraglottic | IV | T4a | N1 | - | + | + |
| HN 386 | 75 | M | OC | Lip | IV | T4 | N2 | - | + | NA |
| HN 389 | 59 | M | OC | Hard palate | IV | T4b | N0 | - | + | + |
| HN 390 | 61 | M | OP | Tonsil | IV | T2 | N3 | + | + | + |
| HN 391 | 54 | M | OP | Unknown | IV | Tx | N2 | + | - | NA |
| HN 392 | 65 | M | OP | Base of tongue | IV | T2 | N2 | + | + | + |
| HN 393 | 83 | M | OP | Base of tongue | IV | T1 | N2 | + | - | NA |
| HN 394 | 51 | M | L | Glottic | IV | T4a | N2 | - | - | NA |
| HN 395 | 55 | M | OP | Tonsil | IV | T4a | N2 | + | + | + |
| HN 396 | 58 | M | OP | Base of tongue | IV | T1 | N2 | + | - | + |
| HN 397 | 55 | M | OP | Tonsil | IV | T2 | N3 | - | - | NA |
| HN 398 | 59 | M | OC | Floor of mouth | III | T1 | N1 | - | + | NA |
| HN 399 | 77 | F | OC | Floor of mouth | I | T1 | N0 | - | + | - |
| HN 400 | 50 | M | OP | Tonsil | IV | T1 | N2 | + | - | + |
| HN 401 | 52 | M | OP | Base of tongue | IV | T2 | N2 | + | + | + |
| HN 402 | 38 | M | OC | Tongue | III | T1 | N1 | - | + | + |
| HN 404 | 65 | F | OP | Tonsil | IV | T2 | N2 | + | - | - |

FIG. 4A

| | | | | | | | | | | |
|---|---|---|---|---|---|---|---|---|---|---|
| HN 405 | 65 | M | H | Post cricoid | IV | T4b | N2 | - | + | + |
| HN 406 | 65 | M | OP | Base of tongue | III | T3 | N0 | - | + | NA |
| HN 407 | 61 | M | L | Transglottic | IV | T4a | N0 | - | + | + |
| HN 408 | 61 | M | OP | Tonsil | I | T1 | N0 | - | + | NA |
| HN 409 | 68 | M | OC | Tongue | IV | T4 | N2 | - | + | NA |
| HN 410 | 58 | M | OP | Tonsil | IV | T1 | N2 | + | + | + |
| HN 411 | 59 | M | OP | Base of tongue | III | T1 | N1 | + | - | + |
| HN 412 | 58 | M | OC | Tongue | III | T3 | N0 | - | + | NA |
| HN 413 | 51 | M | L | Supraglottic | IV | T4a | N2 | - | - | + |
| HN 414 | 59 | M | OP | Base of tongue | III | T2 | N1 | + | + | + |
| HN 415 | 56 | M | OC | Tongue | II | T2 | N0 | + | + | NA |
| HN 416 | 65 | M | OC | Tongue | IV | T4 | N2 | - | + | NA |
| HN 417 | 44 | M | OC | Tongue | IV | T2 | N2 | - | + | NA |
| HN 418 | 73 | F | O | Alveolar ridge | I | T | N | - | + | AN |
| HN 419 | 55 | M | OC | Tongue | VI | T23 | N0 | - | + | NA |
| HN 420 | 40 | M | OC | Tongue | IV | T2 | N2 | - | + | NA |
| HN 421 | 62 | M | OC | Floor of mouth | IV | T4 | N2 | - | + | NA |
| HN 423 | 35 | F | OC | Tongue | IV | T3 | N2 | - | + | NA |
| HN 424 | 50 | M | OC | Tongue | IV | T4a | N0 | - | + | NA |
| HN 425 | 68 | M | OC | Floor of mouth | IV | T3 | N2 | - | + | NA |
| HN 426 | 71 | M | O | Alveolar ridge | I | T4 | N2 | - | + | AN |
| HN 427 | 53 | M | OC | Floor of mouth | IV | T4 | N1 | - | + | AN |
| HN 428 | 58 | F | OC | Tongue | II | T2 | N0 | - | + | AN |
| HN 429 | 61 | F | OC | Tongue | IV | T2 | N2 | - | + | AN |
| HN 430 | 55 | M | OC | Floor of mouth | II | T2 | N0 | - | + | AN |
| HN 431 | 63 | F | OC | Tongue | II | T2 | N0 | - | + | AN |
| HN 432 | 71 | F | OC | Tongue | II | T2 | N0 | - | + | AN |
| HN 433 | 61 | M | O | Alveolar ridge | I | T | N | - | + | AN |
| HN 435 | 67 | M | OC | Retromolar trigone | IV | T4a | N2 | - | + | AN |
| HN 436 | 62 | M | OC | Tongue | IV | T2 | N2 | - | + | AN |
| HN 438 | 56 | F | OC | Tongue | I | T1 | N0 | - | + | NA |
| HN 439 | 65 | M | H | Piriform sinus | IV | T4a | N1 | - | - | + |
| HN 440 | 53 | M | OP | Base of tongue | III | T1 | N1 | + | - | + |
| HN 441 | 80 | F | OP | Tonsil | III | T1 | N1 | + | + | NA |
| HN 443 | 52 | M | OC | Floor of mouth | IV | T4a | N2 | - | + | + |
| HN 444 | 83 | M | OP | Base of tongue | III | T3 | N0 | + | + | NA |
| HN 445 | 74 | F | OC | Tongue | I | T1 | N0 | - | + | - |
| HN 447 | 45 | M | OP | Tonsil | IV | T2 | N2 | + | - | + |
| HN 449 | 52 | M | OP | Tonsil | IV | T3 | N2 | + | + | + |

FIG. 4A Cont

| | | | | | | | | | | |
|---|---|---|---|---|---|---|---|---|---|---|
| HN 450 | 45 | M | OP | Unknown | III | Tx | N1 | + | - | + |
| HN 451 | 82 | M | OC | Tongue | IV | T2 | N2 | - | + | + |
| HN 452 | 60 | M | OP | Base of tongue | IV | T1 | N2 | + | - | + |
| HN 454 | 86 | M | OC | Tongue | IV | T1 | N3 | - | + | NA |
| HN 456 | 60 | M | H | Piriform sinus | IV | T4a | N0 | - | + | + |
| HN 457 | 67 | M | OP | Base of tongue | III | T3 | N1 | - | + | NA |
| HN 458 | 58 | M | L | Glottic | IV | T4a | N0 | - | + | NA |
| HN 459 | 54 | M | OC | Tongue | IV | T3 | N2 | - | + | NA |
| HN 460 | 54 | M | OP | Base of tongue | IV | T2 | N2 | + | - | NA |
| HN 462 | 54 | F | OC | Tongue | IV | T2 | N2 | - | + | NA |
| HN 463 | 68 | M | L | Glottic | I | T1a | N0 | - | + | - |
| HN 464 | 47 | M | OP | Base of tongue | IV | T1 | N2 | + | - | - |
| HN 469 | 58 | M | OP | Tonsil | IV | T2 | N2 | + | + | + |
| HN 473 | 45 | M | OP | Base of tongue | III | T1 | N1 | + | - | NA |
| HN 474 | 39 | M | OP | Base of tongue | IV | T2 | N2 | + | - | NA |

OC = oral cavity, OP = oropharynx, H = hypopharynx, L = larynx, and NA = not available

FIG. 4B

Table S2. Primer sequences used in multiplex assay for identification of driver mutations in tumors.

| Gene | Genomic coordinates of amplified region* | Forward primer Sequence | Reverse primer sequence | Amplicon length (bp) |
|---|---|---|---|---|
| FBXW7 | chr4:153249328-153249457 | GAAGTCCCAACCATGACAAGA | CGGACACTCAAAGTGTGGAA | 130 |
| FBXW7 | chr4:153247295-153247409 | TTGTTTTTCTGTTTCTCCCTCTG | CTGCAACATGACCCATCAAA | 115 |
| FBXW7 | chr4:153247211-153247339 | TTGAGACAGGCCAGTGTTTACAT | CAGTTCTCTGGATCCCACACC | 129 |
| NRAS | chr1:115258719-115258840 | GATGTGGCTCGCCAATTAAC | GATTGTCAGTGCGCTTTTCC | 122 |
| NRAS | chr1:115256485-115256609 | ACACCCCCAGGATTCTTACAG | CGCCTGTCCTCATGTATTGG | 125 |
| PIK3CA | chr3:178916781-178916899 | CCCCTCCATCAACTTCTTC | GAAAAGCCGAAGGTCACAA | 119 |
| PIK3CA | chr3:178921442-178921555 | CAGACGCCATTTCCACAGCTA | ACATTCACGTAGGTTGCACAAA | 114 |
| PIK3CA | chr3:178927879-178928007 | AGAGATGATTGTTGAATTTTCCTTTT | AGTTTATATTTCCCATGCCAAT | 129 |
| PIK3CA | chr3:178951924-178952055 | GCATGCCAATCTCTTCATAAATC | TCCAAAGCCTCTTGCTCAGT | 132 |
| PIK3CA | chr3:178951991-178952119 | TTTGATGACATTGCATACATTCG | GATCCAATCCATTTTGTTGTCCAG | 129 |
| PIK3CA | chr3:178936018-178936140 | CAATGAATTAAGGGAAAATGACAAA | CTCCATTTTAGCACTTACCTGTGAC | 123 |
| HRAS | chr11:534245-534371 | GGCAGGAGACCCTGTAGGAG | GTTCTGGATCAGCTGATGG | 127 |
| HRAS | chr11:533804-533926 | GATGGCAAAACACACAGGA | GTGGTCATTGATGGGAGAAG | 123 |
| CDKN2A | chr9:21971073-21971187 | CCGAGTGGCGGAGCTG | CACCAGCGTGTCCAGGAAG | 115 |
| CDKN2A | chr9:21970874-21971002 | ACAAATTCTCAGATCATCAGTCCTC | AGGAGCTGGGCCATCG | 129 |
| CDKN2A | chr9:21970967-21971091 | GCAGTACCGTGCGACAT | CTTCCTGGACACGCTGGT | 125 |
| CDKN2A | chr9:21971115-21971237 | GGGTCGGGGTGAGAGTGG | TGGCTCTGACCATTCTGTTCT | 123 |
| CDKN2A | chr9:21970997-21971138 | GCTCCCTCAGCCAGTCCA | GACCCCGCCACTCTCAC | 142 |
| CDKN2A | chr9:21974743-21974859 | CACCTCCCTCTACCCGACCC | GGGGAGAGCAGGCAGC | 117 |
| CDKN2A | chr9:21974684-21974798 | GGCCTTCCGACCGTAACTATT | AGCCTTCGCTGACTGG | 115 |
| CDKN2A | chr9:21974652-21974761 | CTCCCGCTGCAGACCCT | GGGTCGGGTAGAGGAGGTG | 110 |
| CDKN2A | chr9:21968163-21968300 | CTGTAGGACCTTCGGTGACTG | TGTGCCACACATCTTTGACC | 138 |

FIG. 5

| Gene | Coordinates | Sequence | Length |
|---|---|---|---|
| TP53 | chr17:7579818-7579933 | CCTTCCAATGGATCCACTCAC | ACTGCCTTCCGGGTCACT | 116 |
| TP53 | chr17:7579679-7579789 | AGCCCCCTAGCAGAGACCT | CAGCCCAACCCTTGTCCTT | 111 |
| TP53 | chr17:7579502-7579616 | TGACTGCTCTTTTCACCCATC | TCATCTGGACCTGGGTCTTC | 115 |
| TP53 | chr17:7579441-7579572 | GCAATGCGATGATTTGATGCTG | CGGTGTAGGAGCTGCTGG | 132 |
| TP53 | chr17:7579388-7579501 | AGTCCCAGAATGCCAGAG | TGGGAAGGGACAGAAGATGA | 114 |
| TP53 | chr17:7579338-7579463 | CTGCACCAGCAGCTCCTAC | CAGAATGCAAGAAGCCCAGA | 126 |
| TP53 | chr17:7579270-7579396 | GCATTGAAGTCTCATGGAAGC | CCCTTCCAGAAAAACCTACC | 127 |
| TP53 | chr17:7578475-7578593 | GCCCTGACTTTCAACTCTGTCT | GGGGGTGTGAATCAACC | 119 |
| TP53 | chr17:7578417-7578540 | CTCCGTCATGTGCTGTGACT | CAACAAGATGTTTTGCCAACTG | 124 |
| TP53 | chr17:7578335-7578455 | GCCATGGCCATCTACAAGC | ACCAGCCCTGTCGTCTC | 121 |
| TP53 | chr17:7578211-7578326 | GTCCCCAGGCCTCTGATT | CGAAAAGTGTTTCTGTCATCCA | 116 |
| TP53 | chr17:7578137-7578260 | GTGGAAGGAAATTTGCGTGT | CTTAACCCCTCCTCCCAGAG | 124 |
| TP53 | chr17:7577513-7577635 | TGTGATGATGGTGAGGATGG | TCATCTGGCCTGTGTTATC | 123 |
| TP53 | chr17:7577480-7577606 | TGGCTCTGACTGTACCACCATC | GTGGCAAGTGGCTCCTGA | 127 |
| TP53 | chr17:7577068-7577188 | TGCCTCTTGCTTCTCTTTTCC | GCGGAGATTCTCTTCCTCTGT | 121 |
| TP53 | chr17:7576997-7577121 | CGTGTTTGTGCCTGTCCTG | GCTTCTTGTCCTGCTTGCTT | 125 |
| TP53 | chr17:7576840-7576956 | TTTTATCACCTTTCCTTGCCTCT | CAAGACTTAGTACCTGAAGGGTGAA | 117 |
| TP53 | chr17:7576782-7576898 | AAGAAGAAAACGGCATTTTGAG | CCAGCCAAAGAAGAAACCAC | 117 |
| TP53 | chr17:7573947-7574059 | CCCTGGCTCCTTCCCAG | CTTCTCCCCCTCCTCTGTTG | 113 |
| TP53 | chr17:7573881-7574007 | GTTCCCAGAGCTGAATGAGG | TAGGAAGGCAGGGAGTAGG | 127 |
| TP53 | chr17:7572929-7573043 | AGTCTGAGTCAGGCCCTTCTG | ATGTCATCTCTCCTCCCTGCT | 115 |
| TP53 | chr17:7572929-7573043 | ATGTCATCTCTCCTCCCTGCT | AGTCTGAGTCAGGCCCTTCTG | 115 |
| TP53 | chr17:7572893-7573009 | GCCACCTGAAGTCCAAAAAG | GAGGCTGTCAGTGGGGAAC | 117 |

*Coordinates refer to the human reference genome hg19 release (Genome Reference Consortium GRCh37, Feb 2009).

FIG. 5 Cont

Table S3: Levels of Tumor-derived DNA in Saliva and Plasma

| PATIENT | | | | | |
|---|---|---|---|---|---|
| Patient ID | Interval between Biopsy and Sample Collection (days) | Treatment Prior to Sample Collection for Patients with Recurrence (days prior) | Site | HPV status of Tumor | Gene mutated in Tumor |
| HN 358 | 78 | No prior treatment | OC | HPV negative | TP53 |
| HN 359 | 335 | RT (449) | L | HPV negative | TP53 |
| HN 361 | 29 | No prior treatment | OC | HPV negative | TP53 |
| HN 362 | 66 | No prior treatment | OP | HPV16 positive | PIK3CA |
| HN 363 | 24 | Surgery (151) | OC | HPV negative | TP53 |
| HN 364 | 21 | Surgery, RT (324) | OC | HPV negative | TP53 |
| HN 365 | 28 | CRT (244) | OP | HPV16 positive | HPV16 |
| HN 366 | 35 | No prior treatment | OC | HPV negative | TP53 |
| HN 367 | 24 | CRT (774) | OP | HPV16 positive | PIK3CA |
| HN 368 | 15 | No prior treatment | OC | HPV negative | TP53 |
| HN 369 | 20 | RT (190) | L | HPV negative | TP53 |
| HN 370 | 34 | No prior treatment | OC | HPV negative | TP53 |
| HN 371 | 40 | No prior treatment | OC | HPV negative | NOTCH1 |
| HN 372 | 75 | Surgery, RT (3503) | OP | HPV negative | TP53 |
| HN 373 | No prior biopsy | CRT (161) | L | HPV negative | TP53 |
| HN 375 | 42 | No prior treatment | OC | HPV negative | TP53 |
| HN 377 | No prior biopsy | Surgery (709) | OP | HPV16 positive | HPV16 |
| HN 380 | 27 | CRT (432) | L | HPV negative | TP53 |
| HN 381 | 32 | CRT (194) | OC | HPV negative | TP53 |
| HN 382 | 14 | No prior treatment | OC | HPV negative | TP53 |
| HN 383 | 26 | No prior treatment | OC | HPV negative | TP53 |
| HN 384 | 49 | No prior treatment | OP | HPV16 positive | PIK3CA |
| HN 385 | 93 | No prior treatment | L | HPV negative | TP53 |
| HN 386 | 84 | Surgery (1249) | OC | HPV negative | TP53 |
| HN 389 | 35 | No prior treatment | OC | HPV negative | PIK3CA |
| HN 390 | 33 | No prior treatment | OP | HPV16 positive | HPV16 |
| HN 391 | 48 | No prior treatment | OP | HPV16 positive | HPV16 |
| HN 392 | 9 | No prior treatment | OP | HPV16 positive | FBXW7 |
| HN 393 | 28 | No prior treatment | OP | HPV16 positive | HPV16 |
| HN 394 | 27 | RT (337) | L | HPV negative | TP53 |
| HN 395 | 23 | No prior treatment | OP | HPV16 positive | HPV16 |
| HN 396 | 9 | No prior treatment | OP | HPV16 positive | PIK3CA |

Fig. 6A

| | | | | |
|---|---|---|---|---|
| HN 397 | 42 | No prior treatment | OP | HPV negative | TP53 |
| HN 398 | 23 | No prior treatment | OC | HPV negative | NA |
| HN 399 | No prior biopsy | No prior treatment | OC | HPV negative | TP53 |
| HN 400 | 18 | No prior treatment | OP | HPV16 positive | PIK3CA |
| HN 401 | 23 | CRT (226) | OP | HPV16 positive | HPV16 |
| HN 402 | 35 | No prior treatment | OC | HPV negative | TP53 |
| HN 404 | 36 | No prior treatment | OP | HPV16 positive | NRAS |
| HN 405 | 53 | No prior treatment | H | HPV negative | TP53 |
| HN 406 | 21 | No prior treatment | OP | HPV negative | TP53 |
| HN 407 | 20 | No prior treatment | L | HPV negative | TP53 |
| HN 408 | 42 | Surgery, RT (1783) | OP | HPV negative | TP53 |
| HN 409 | 28 | No prior treatment | OC | HPV negative | CDKN2A |
| HN 410 | 25 | No prior treatment | OP | HPV16 positive | HPV16 |
| HN 411 | 78 | No prior treatment | OP | HPV16 positive | HPV16 |
| HN 412 | 20 | No prior treatment | OC | HPV negative | NA |
| HN 413 | 109 | No prior treatment | L | HPV negative | TP53 |
| HN 414 | 22 | Surgery, RT (3757) | OP | HPV16 positive | PIK3CA |
| HN 415 | 69 | No prior treatment | OC | HPV16 positive | HPV16 |
| HN 416 | 25 | No prior treatment | OC | HPV negative | NOTCH1 |
| HN 417 | 58 | No prior treatment | OC | HPV negative | TP53 |
| HN 418 | 74 | No prior treatment | OC | HPV negative | TP53 |
| HN 419 | 22 | No prior treatment | OC | HPV negative | TP53 |
| HN 420 | 31 | No prior treatment | OC | HPV negative | TP53 |
| HN 421 | 68 | No prior treatment | OC | HPV negative | NOTCH1 |
| HN 423 | 35 | No prior treatment | OC | HPV negative | TP53 |
| HN 424 | 107 | No prior treatment | OC | HPV negative | TP53 |
| HN 425 | 36 | No prior treatment | OC | HPV negative | TP53 |
| HN 426 | 31 | No prior treatment | OC | HPV negative | CDKN2A |
| HN 427 | 45 | No prior treatment | OC | HPV negative | TP53 |
| HN 428 | 55 | No prior treatment | OC | HPV negative | TP53 |
| HN 429 | 58 | No prior treatment | OC | HPV negative | TP53 |
| HN 430 | 49 | No prior treatment | OC | HPV negative | TP53 |
| HN 431 | 39 | No prior treatment | OC | HPV negative | NOTCH1 |
| HN 432 | 58 | No prior treatment | OC | HPV negative | TP53 |
| HN 433 | 49 | Surgery, CRT (1095) | OC | HPV negative | TP53 |
| HN 435 | 77 | No prior treatment | OC | HPV negative | TP53 |
| HN 436 | 52 | No prior treatment | OC | HPV negative | TP53 |
| HN 438 | 22 | No prior treatment | OC | HPV negative | TP53 |

| | | | | |
|---|---|---|---|---|
| HN 439 | 49 | No prior treatment | HPV negative | TP53 |
| HN 440 | 52 | No prior treatment | HPV16 positive | HPV16 |
| HN 441 | 62 | No prior treatment | HPV16 positive | HPV16 |
| HN 443 | 87 | No prior treatment | HPV negative | TP53 |
| HN 444 | 56 | Surgery, RT (2279) | HPV16 positive | PIK3CA |
| HN 445 | 25 | No prior treatment | HPV negative | PIK3CA |
| HN 447 | 8 | No prior treatment | HPV16 positive | HPV16 |
| HN 449 | 29 | No prior treatment | HPV16 positive | FBXW7 |
| HN 450 | 48 | No prior treatment | HPV16 positive | HPV16 |
| HN 451 | No prior biopsy | CRT (157) | HPV negative | TP53 |
| HN 452 | 90 | No prior treatment | HPV16 positive | FBXW7 |
| HN 454 | 23 | No prior treatment | HPV negative | TP53 |
| HN 456 | 26 | RT (121) Surgery, | HPV negative | TP53 |
| HN 457 | 18 | RT (4729) No prior | HPV negative | TP53 |
| HN 458 | 40 | treatment Surgery, | HPV negative | TP53 |
| HN 459 | 22 | RT (69) No prior | HPV negative | TP53 |
| HN 460 | 37 | treatment No prior | HPV16 positive | PIK3CA |
| HN 462 | 41 | treatment No prior | HPV negative | TP53 |
| HN 463 | No prior biopsy | treatment No prior | HPV negative | TP53 |
| HN 464 | 28 | treatment No prior | HPV16 positive | HPV16 |
| HN 469 | 58 | treatment No prior | HPV16 positive | HPV16 |
| HN 473 | 11 | treatment No prior | HPV16 positive | HPV16 |
| HN 474 | 44 | treatment | HPV16 positive | HPV16 |

Patients in BOLD had both saliva and plasma available. RT = Radiation therapy, CRT = Chemoradiation therapy

Fig. 6D

TUMOR

| Type of Mutation | Genomic Position | cDNA Change | Amino Acid Change | Somatic Mutation: Patient FRACTION of MUTANT reads |
|---|---|---|---|---|
| SBS | 7578524 | 406C>T | Q136* | 0.541% |
| SBS | 7577082 | 856G>A | E286K | 0.009% |
| SBS | 7578268 | 581T>G | L194R | 0.245% |
| SBS | 178936091 | 1633G>A | E545K | 0.000% |
| SBS | 7576851 | c.993+2T>C | NA | 5.443% |
| SBS | 7576928 | c.920-2A>G | NA | 0.106% |
| NA | NA | NA | NA | Only HPV assessed |
| SBS | 7578553 | 377A>G | Y126C | 3.296% |
| SBS | 178936082 | 1624G>A | E542K | 0.003% |
| SBS | 7578550 | 380C>A | S127Y | 11.467% |
| INDEL | 7577094 | c.844_845insCTGTGCGCC | R282fs | 0.001% |
| SBS | 7577094 | 844C>T | R282W | 2.390% |
| SBS | 139411837 | 1442G>T | G481V | 1.628% |
| SBS | 7577120 | 818G>T | R273L | 0.007% |
| SBS | 7574021 | 1006G>T | E336* | 0.000% |
| SBS | 7575574 | 707A>G | Y236C | 0.040% |
| NA | NA | NA | NA | Only HPV assessed |
| SBS | 7577082 | 856G>A | E286K | 0.026% |
| SBS | 7577097 | 841G>A | D281N | 0.282% |
| SBS | 7577370 | 711G>A | M237I | 6.120% |
| SBS | 7577094 | 844C>T | R282W | 0.190% |
| SBS | 178936091 | 1633G>A | E545K | 0.000% |
| SBS | 7579358 | 329G>T | R110L | 0.004% |
| SBS | 7578500 | 430C>T | Q144* | 0.168% |
| SBS | 178952085 | 3140A>G | H1047R | 3.497% |
| NA | NA | NA | NA | Only HPV assessed |
| NA | NA | NA | NA | Only HPV assessed |
| SBS | 153249384 | 1394C>T | R465H | 0.005% |
| NA | NA | NA | NA | Only HPV assessed |
| SBS | 7578179 | 670G>T | E224* | 0.000% |
| NA | NA | NA | NA | Only HPV assessed |
| SBS | 178916876 | 263G>A | R88Q | 0.000% |

| Type | Position | Mutation | Protein | Frequency |
|---|---|---|---|---|
| SBS | 7578478 | 452C>A | P151H | 0.000% |
| Translocation | chr11:69467879-chr11:69469070 | NA | NA | 43.000% |
| SBS | 7577121 | 817C>T | R273C | 1.850% |
| SBS | 178936091 | 1633G>A | E545K | 0.000% |
| NA | NA | NA | NA | Only HPV assessed |
| SBS | 7577120 | 818G>A | R273H | 0.027% |
| SBS | 115256530 | 181C>A | Q61K | 0.000% |
| SBS | 7577538 | 743G>A | R248Q | 0.033% |
| SBS | 7574000 | 1027G>T | E343* | 0.005% |
| SBS | 7578406 | 524G>A | R175H | 0.024% |
| SBS | 7577568 | 713G>T | C238F | 0.006% |
| INDEL | 21971125-21971127 | 231delTC | T77fs | 0.028% |
| NA | NA | NA | NA | Only HPV assessed |
| NA | NA | NA | NA | Only HPV assessed |
| Translocation | chr18:45662870-chr11:69291050 | NA | NA | 41.000% |
| SBS | 7577538 | 743G>T | R248L | 0.000% |
| SBS | 178936082 | 1624G>A | E542K | 0.000% |
| NA | NA | NA | NA | Only HPV assessed |
| INDEL | 139396749 | 5359delC | L1787fs | 0.060% |
| SBS | 7578406 | 524G>A | R175H | 0.560% |
| SBS | 7577538 | 743G>A | R248Q | 6.097% |
| SBS | 7578271 | 578A>T | H193L | 0.217% |
| SBS | 7574003 | 1024C>T | R342* | 7.347% |
| INDEL | 139418317 | 255_256insA | Y85fs | 3.469% |
| SBS | 7577081 | 857A>C | E286A | 2.104% |
| SBS | 7577046 | 892G>T | E298* | 0.653% |
| INDEL | 7577498 | c.782+1_782+2insC | NA | 0.068% |
| SBS | 21968242 | c.458-1G>A | NA | 1.744% |
| SBS | 7578392 | 538G>T | E180* | 0.559% |
| SBS | 7577121 | 817C>T | R273C | 1.086% |
| SBS | 7577574 | 707A>G | Y236C | 2.072% |
| SBS | 7578212 | 637C>T | R213* | 0.759% |
| SBS | 7574017 | 1010G>T | R337L | 1.263% |
| SBS | 7577118 | 820G>T | V274F | 1.430% |
| SBS | 7578458 | 472C>G | R158G | 0.204% |
| SBS | 7578550 | 380C>A | S127Y | 2.200% |
| SBS | 7579366 | 321C>G | Y107* | 0.880% |
| SBS | 7577590 | 691A>G | T231A | 0.062% |

| Type | ID | Mutation | Protein | Frequency |
|---|---|---|---|---|
| SBS | 7578188 | 661G>T | E221* | 0.000% |
| NA | NA | NA | NA | Only HPV assessed |
| NA | NA | NA | NA | Only HPV assessed |
| INDEL | 7579590 | 97-2_97delAGT | S33fs | 0.570% |
| SBS | 178936082 | 1624G>A | E542K | 0.020% |
| SBS | 178952085 | 3140A>G | H1047R | 0.151% |
| NA | NA | NA | NA | Only HPV assessed |
| SBS | 152249384 | 1394C>T | R465H | 0.019% |
| NA | NA | NA | NA | Only HPV assessed |
| SBS | 7577094 | 844C>T | R282W | 0.419% |
| SBS | 152247289 | 1513C>G | R505G | 0.000% |
| SBS | 7578492 | 438G>A | W146* | 0.121% |
| SBS | 7574018 | 1009C>T | R337C | 0.020% |
| SBS | 7579358 | 329G>T | R110L | 0.113% |
| SBS | 7577121 | 817C>T | R273C | 0.106% |
| SBS | 7578271 | 578A>G | H193R | 0.076% |
| SBS | 178936091 | 1633G>A | E545K | 0.000% |
| SBS | 7578492 | 438G>A | W146* | 0.073% |
| SBS | 7578208 | 641A>G | H214R | 0.015% |
| NA | NA | NA | NA | Only HPV assessed |
| NA | NA | NA | NA | Only HPV assessed |
| NA | NA | NA | NA | Only HPV assessed |
| NA | NA | NA | NA | Only HPV assessed |

Fig. 6G

| Somatic Mutation: Patient NUMBER of MUTANT reads | Somatic Mutation: Patient NUMBER of WILD-TYPE reads | Somatic Mutation: CONTROL FRACTION of MUTANT reads |
|---|---|---|
| 657 | 120798 | 0.000% |
| 19 | 205715 | 0.000% |
| 845 | 343819 | 0.004% |
| 0 | 32958 | 0.000% |
| 8843 | 153613 | 0.001% |
| 189 | 177609 | 0.001% |
| Only HPV assessed | Only HPV assessed | Only HPV assessed |
| 4905 | 143907 | 0.000% |
| 28 | 862561 | 0.000% |
| 22073 | 170413 | 0.002% |
| 10 | 1190330 | 0.000% |
| 9233 | 377059 | 0.006% |
| 9504 | 574434 | 0.000% |
| 29 | 426931 | 0.000% |
| 0 | 79917 | 0.000% |
| 123 | 310509 | 0.000% |
| Only HPV assessed | Only HPV assessed | Only HPV assessed |
| 107 | 414013 | 0.000% |
| 911 | 322360 | 0.000% |
| 20130 | 308811 | 0.000% |
| 394 | 207299 | 0.006% |
| 0 | 33081 | 0.000% |
| 29 | 717919 | 0.000% |
| 166 | 98840 | 0.011% |
| 5130 | 141558 | 0.000% |
| Only HPV assessed | Only HPV assessed | Only HPV assessed |
| Only HPV assessed | Only HPV assessed | Only HPV assessed |
| 8 | 165676 | 0.000% |
| Only HPV assessed | Only HPV assessed | Only HPV assessed |
| 0 | 111372 | 0.000% |
| Only HPV assessed | Only HPV assessed | Only HPV assessed |
| 0 | 248376 | 0.000% |

SALIVA

| | | | |
|---|---|---|---|
| 0 | 174729 | | 0.000% |
| 4301 | 5701 | | 0.000% |
| 5696 | 302191 | | 0.014% |
| 0 | 44937 | | 0.000% |
| Only HPV assessed | Only HPV assessed | | Only HPV assessed |
| 90 | 336318 | | 0.000% |
| 0 | 435825 | | 0.000% |
| 57 | 175443 | | 0.001% |
| 22 | 446306 | | 0.000% |
| 94 | 398354 | | 0.004% |
| 18 | 294486 | | 0.001% |
| 102 | 370428 | | 0.000% |
| Only HPV assessed | Only HPV assessed | | Only HPV assessed |
| Only HPV assessed | Only HPV assessed | | Only HPV assessed |
| 4099 | 5899 | | 0.000% |
| 0 | 139509 | | 0.000% |
| 0 | 118473 | | 0.000% |
| Only HPV assessed | Only HPV assessed | | Only HPV assessed |
| 98 | 164341 | | 0.000% |
| 698 | 123940 | | 0.011% |
| 19333 | 297749 | | 0.006% |
| 302 | 139354 | | 0.000% |
| 32586 | 410934 | | 0.004% |
| 9920 | 276064 | | 0.000% |
| 3222 | 149904 | | 0.000% |
| 2935 | 446813 | | 0.000% |
| 253 | 374009 | | 0.000% |
| 842 | 47438 | | 0.002% |
| 390 | 69396 | | 0.003% |
| 2141 | 195085 | | 0.009% |
| 188 | 8878 | | 0.000% |
| 968 | 126514 | | 0.012% |
| 4979 | 389245 | | 0.001% |
| 1870 | 128915 | | 0.000% |
| 119 | 58051 | | 0.000% |
| 3592 | 159698 | | 0.000% |
| 2415 | 272049 | | 0.000% |
| 210 | 340200 | | 0.001% |

| Somatic Mutation: CONTROL NUMBER of MUTANT reads | Somatic Mutation: CONTROL NUMBER of WILD-TYPE reads | Somatic Mutation: P-value (Patient vs. Control) |
|---|---|---|
| 0 | 78462 | 3.00E-94 |
| 0 | 190784 | 7.25E-05 |
| 6 | 137370 | 5.81E-72 |
| 0 | 99828 | NA |
| 3 | 244530 | 0.00E+00 |
| 2 | 285252 | 7.88E-66 |
| Only HPV assessed | Only HPV assessed | NA |
| 0 | 78462 | 0.00E+00 |
| 0 | 165648 | 1.66E-02 |
| 4 | 229130 | 0.00E+00 |
| 0 | 3671899 | 7.73E-07 |
| 6 | 94302 | 0.00E+00 |
| 0 | 74781 | 2.77E-270 |
| 2 | 523939 | 1.40E-07 |
| 0 | 75699 | NA |
| 0 | 222409 | 1.49E-20 |
| Only HPV assessed | Only HPV assessed | NA |
| 0 | 304190 | 1.81E-18 |
| 0 | 94302 | 1.37E-59 |
| 6 | 73755 | 0.00E+00 |
| 0 | 94302 | 2.01E-37 |
| 0 | 99828 | NA |
| 6 | 297066 | 1.11E-03 |
| 4 | 36747 | 7.42E-13 |
| 0 | 132561 | 0.00E+00 |
| Only HPV assessed | Only HPV assessed | NA |
| Only HPV assessed | Only HPV assessed | NA |
| 0 | 113715 | 2.48E-02 |
| Only HPV assessed | 8730 | NA |
| 0 | Only HPV assessed | NA |
| Only HPV assessed | 75132 | NA |

Fig. 6K

| | | |
|---|---|---|
| 0 | 36747 | NA |
| 0 | 9998 | NA |
| 14 | 101826 | 0.00E+00 |
| 0 | 99828 | NA |
| Only HPV assessed | Only HPV assessed | NA |
| 0 | 101826 | 3.49E-07 |
| 0 | 96993 | NA |
| 1 | 73755 | 6.60E-06 |
| 0 | 151305 | 1.29E-02 |
| 8 | 189739 | 2.35E-07 |
| 2 | 222409 | 5.83E-03 |
| 0 | 62736 | 5.93E-05 |
| Only HPV assessed | Only HPV assessed | NA |
| Only HPV assessed | Only HPV assessed | NA |
| 0 | 11051 | NA |
| 0 | 73755 | NA |
| 0 | 99828 | NA |
| Only HPV assessed | Only HPV assessed | NA |
| 0 | 12387 | 1.17E-02 |
| 16 | 140283 | 2.58E-162 |
| 12 | 215316 | 0.00E+00 |
| 0 | 243910 | 3.26E-116 |
| 14 | 323181 | 0.00E+00 |
| 0 | 52392 | 0.00E+00 |
| 0 | 94302 | 0.00E+00 |
| 0 | 94302 | 2.58E-136 |
| 0 | 213470 | 6.50E-33 |
| 2 | 103908 | 0.00E+00 |
| 4 | 140283 | 9.79E-169 |
| 25 | 274420 | 0.00E+00 |
| 0 | 177032 | 0.00E+00 |
| 21 | 182440 | 2.16E-288 |
| 3 | 323181 | 0.00E+00 |
| 0 | 101826 | 0.00E+00 |
| 0 | 36747 | 9.36E-18 |
| 0 | 78462 | 0.00E+00 |
| 0 | 250810 | 0.00E+00 |
| 3 | 215316 | 1.04E-28 |

| HPV: templates/ng DNA | Somatic Mutation: Patient FRACTION of MUTANT reads | Somatic Mutation: Patient NUMBER of MUTANT reads |
|---|---|---|
| Not quantified | 0.000% | 0 |
| Not quantified | 0.019% | 54 |
| Not quantified | 0.017% | 21 |
| No HPV templates found | No plasma available | No plasma available |
| Not quantified | 0.796% | 1999 |
| Not quantified | 0.901% | 1831 |
| 59.8 | Only HPV assessed | Only HPV assessed |
| Not quantified | 0.582% | 674 |
| No HPV templates found | 0.423% | 379 |
| Not quantified | 0.867% | 338 |
| Not quantified | No plasma available | No plasma available |
| Not quantified | 0.498% | 251 |
| Not quantified | No plasma available | No plasma available |
| Not quantified | 0.082% | 63 |
| Not quantified | 0.092% | 173 |
| No HPV templates found | No plasma available | No plasma available |
| Not quantified | Only HPV assessed | Only HPV assessed |
| Not quantified | 1.379% | 415 |
| Not quantified | 1.852% | 854 |
| Not quantified | No plasma available | No plasma available |
| No HPV templates found | 0.031% | 5 |
| Not quantified | 0.022% | 19 |
| Not quantified | 0.089% | 116 |
| Not quantified | No plasma available | No plasma available |
| 0.6 | 0.022% | 97 |
| No HPV templates found | Only HPV assessed | Only HPV assessed |
| 0.3 | No plasma available | No plasma available |
| No HPV templates found | 0.638% | 770 |
| Not quantified | No plasma available | No plasma available |
| 54.1 | Only HPV assessed | Only HPV assessed |
| No HPV templates found | 0.344% | 331 |

Fig. 6M

PLASMA

| Somatic Mutation: Patient NUMBER of WILD-TYPE reads | Somatic Mutation: CONTROL FRACTION of MUTANT reads | Somatic Mutation: CONTROL NUMBER of MUTANT reads |
|---|---|---|
| 69216 | 0.000% | 0 |
| 282174 | 0.002% | 3 |
| 120144 | 0.001% | 3 |
| No plasma available | No plasma available | No plasma available |
| 251160 | 0.000% | 0 |
| 203268 | 0.000% | 0 |
| Only HPV assessed | Only HPV assessed | Only HPV assessed |
| 115812 | 0.000% | 0 |
| 89622 | 0.000% | 0 |
| 39024 | 0.000% | 0 |
| No plasma available | No plasma available | No plasma available |
| 50454 | 0.010% | 10 |
| No plasma available | No plasma available | No plasma available |
| 76758 | 0.000% | 0 |
| 187566 | 0.000% | 0 |
| No plasma available | No plasma available | No plasma available |
| Only HPV assessed | Only HPV assessed | Only HPV assessed |
| 30132 | 0.002% | 3 |
| 46104 | 0.000% | 0 |
| No plasma available | No plasma available | No plasma available |
| 16158 | 0.004% | 5 |
| 87564 | 0.000% | 0 |
| 130764 | 0.000% | 0 |
| No plasma available | No plasma available | No plasma available |
| 440478 | 0.000% | 0 |
| Only HPV assessed | Only HPV assessed | Only HPV assessed |
| No plasma available | No plasma available | No plasma available |
| 120570 | 0.004% | 5 |
| No plasma available | No plasma available | No plasma available |
| No plasma available | No plasma available | No plasma available |
| Only HPV assessed | Only HPV assessed | Only HPV assessed |
| 96294 | 0.011% | 26 |

Fig. 6P

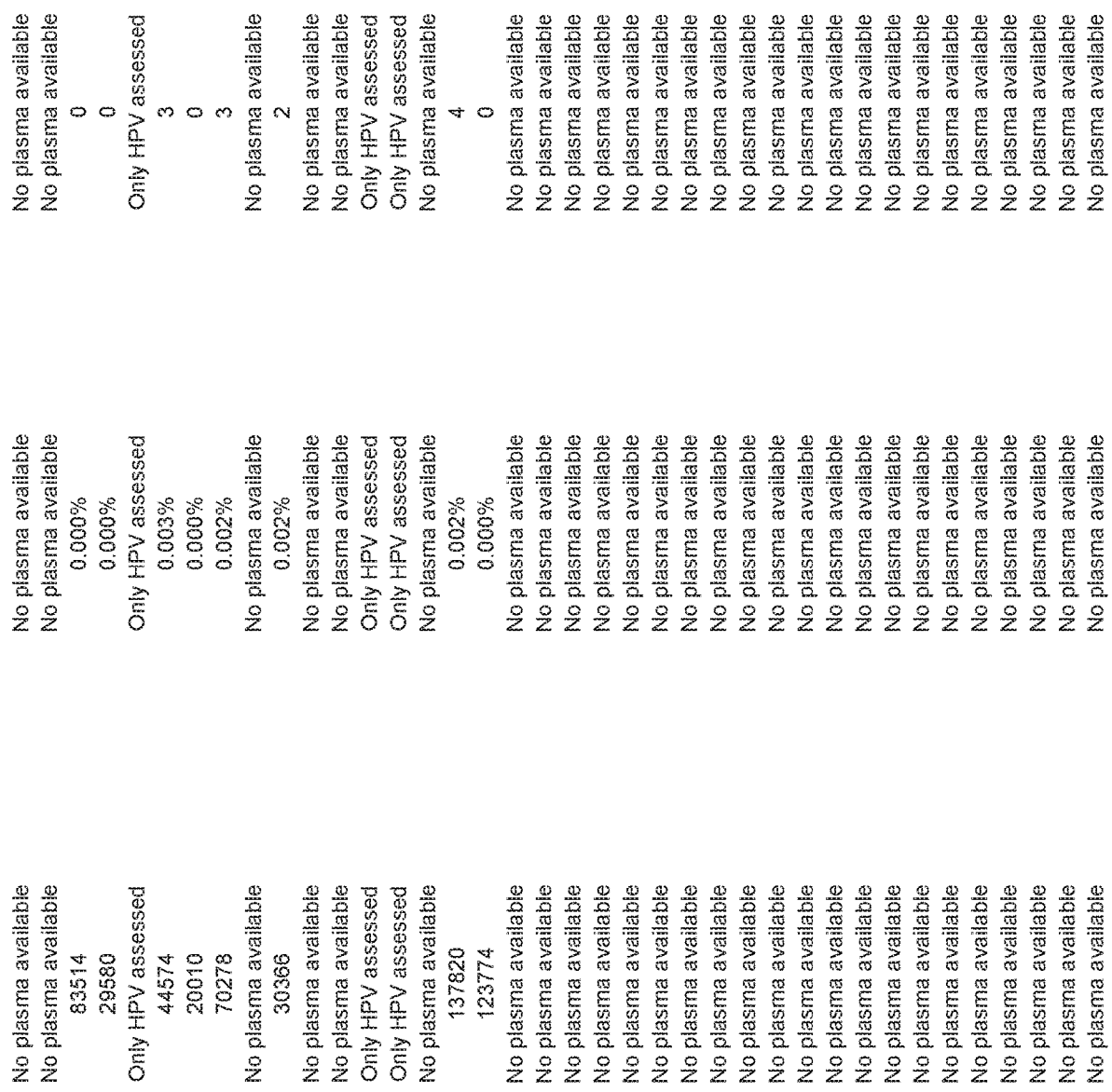

Fig. 6S

| Somatic Mutation: CONTROL NUMBER of WILD-TYPE reads | Somatic Mutation: P-value (Patient vs. Control) | HPV: templates/ng DNA |
|---|---|---|
| 81680 | NA | Not quantified |
| 128972 | 4.05E-05 | Not quantified |
| 292883 | 1.24E-09 | Not quantified |
| No plasma available | NA | No plasma available |
| 143400 | 3.89E-249 | No HPV templates found |
| 162245 | 0.00E+00 | No HPV templates found |
| Only HPV assessed | NA | 63 |
| 108590 | 1.19E-138 | Not quantified |
| 155200 | 8.88E-144 | 45.5 |
| 108590 | 1.95E-204 | No HPV templates found |
| No plasma available | NA | No plasma available |
| 96060 | 6.68E-97 | Not quantified |
| No plasma available | NA | No plasma available |
| 118580 | 2.16E-22 | Not quantified |
| 148060 | 3.80E-31 | Not quantified |
| No plasma available | NA | No plasma available |
| Only HPV assessed | NA | 6386.6 |
| 128972 | 0.00E+00 | No HPV templates found |
| 96070 | 0.00E+00 | No HPV templates found |
| No plasma available | NA | No plasma available |
| 140730 | 1.87E-03 | Not quantified |
| 155200 | 2.64E-08 | 8.9 |
| 148650 | 4.82E-30 | Not quantified |
| No plasma available | NA | No plasma available |
| 166610 | 2.79E-09 | Not quantified |
| Only HPV assessed | NA | 4 |
| No plasma available | NA | No plasma available |
| 126570 | 1.64E-173 | 33.1 |
| No plasma available | NA | No plasma available |
| No plasma available | NA | No plasma available |
| Only HPV assessed | NA | 57.8 |
| 235469 | 7.38E-154 | 369.2 |

| | | |
|---|---|---|
| No plasma available | NA | No plasma available |
| No plasma available | NA | No plasma available |
| 556028 | NA | Not quantified |
| 155200 | 5.36E-94 | No HPV templates found |
| Only HPV assessed | NA | 126.2 |
| 118577 | 1.10E-05 | Not quantified |
| 136300 | NA | No HPV templates found |
| 162792 | 1.19E-18 | Not quantified |
| No plasma available | NA | No plasma available |
| 105793 | 7.69E-03 | Not quantified |
| No plasma available | NA | No plasma available |
| No plasma available | NA | No plasma available |
| Only HPV assessed | NA | 12.3 |
| Only HPV assessed | NA | 1.1 |
| No plasma available | NA | No plasma available |
| 162791 | 1.74E-115 | Not quantified |
| 155200 | 9.26E-69 | 20.7 |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |
| No plasma available | NA | No plasma available |

| | | |
|---|---|---|
| 153345 Only HPV assessed No plasma available | 0.00E+00 | Not quantified |
| | NA | 3.4 |
| 123775 No plasma available | NA | No plasma available Not quantified |
| | 2.07E-18 | No plasma available Not quantified |
| 166610 Only HPV assessed | NA | |
| | NA | 11.8 |
| 126570 Only HPV assessed | NA | 67.4 |
| | 6.40E-20 | 7.9 |
| 96060 | NA | No HPV templates found |
| | 3.07E-177 | 13.7 |
| 227918 No plasma available | 6.51E-34 | No plasma available No HPV templates found No plasma available No plasma available |
| 148050 | NA | |
| | 0.00E+00 | |
| No plasma available No plasma available No plasma available No plasma available No plasma available | NA NA NA NA | No plasma available No plasma available Not quantified No HPV templates found |
| 153345 Only HPV assessed Only HPV assessed No plasma available No plasma available | NA NA NA | |
| | NA | 4.5 |
| | NA | No plasma available No plasma available |
| | NA | |

HEAD AND NECK SQUAMOUS CELL CARCINOMA ASSAYS

CROSS-REFERENCE TO RELATED APPLICATIONS

This application is a National Stage Application under 35 U.S.C. § 371 and claims the benefit of International Application No. PCT/US2016/037793, filed Jun. 16, 2016, which claims the benefit of U.S. Provisional Application No. 62/182,757, filed Jun. 22, 2015. The disclosures of the foregoing applications are hereby incorporated by reference in their entireties.

This invention was made with government support under CA043460, CA057345, and DE019032 awarded by NIH. The government has certain rights in the invention.

TECHNICAL FIELD OF THE INVENTION

This invention is related to the area of cancer. In particular, it relates to assays for cancer.

BACKGROUND OF THE INVENTION

Head and neck squamous cell carcinomas (HNSCC) are the $7^{th}$ most common cancer worldwide, occurring in more than half a million new patients each year and >50,000 patients in the United States alone (1, 2). The incidence of certain types of HNSCC appears to be increasing, especially among young people, in part due to the increasing prevalence of human papilloma virus (HPV) (3-7). HNSCCs are associated with a poor five-year overall survival of only ~50% that has remained relatively unchanged, especially for patients with HPV-negative tumors (8). Only a few targeted therapies for this disease are available, in part because of the paucity of activating mutations in oncogenes that contribute to tumor development; most genetic alterations in HNSCCs inactivate tumor suppressor genes (9-12). There are also no available biomarkers for HNSCC to measure disease burden or response to therapy, further limiting progress in mitigating the impact of this often morbid and potentially lethal disease on human health.

Though HNSCC tumors are usually classified based on histology, their biomedical properties, including demographics, risks factors, and clinical behavior, differ by anatomic site (FIG. 1) (13, 14). Anatomically, the tumors are categorized as squamous cell carcinomas (SCC) of the oral cavity (including the oral tongue), oropharynx (including the base of the tongue), larynx, and hypopharynx. Oral cavity SCC, with the exception of those of the oral tongue, is declining in incidence in the United States due to the reduction in cigarette smoking (4). In contrast, there is an increasing incidence of oropharyngeal SCC involving the palatine and lingual (base of tongue) tonsils, particularly in younger men. These tumors are often associated with HPV. The survival of these patients is better than for those whose tumors are unassociated with HPV (6, 15). Laryngeal SCC is declining in incidence and, unlike HNSCC at other sites, is generally associated with limited regional metastasis due to anatomic barriers (16). The hypopharynx is the least common site for HNSCC and has decreasing incidence but relatively poor prognosis (17, 18).

The idea that the genetic alterations present in tumors can be used as biomarkers for cancer was proposed more than two decades ago (19-22). The advantage of genetic alterations over conventional biomarkers such as carcinoembryonic antigen (CEA) or prostate specific antigen (PSA) is that genetic changes are exquisitely specific for neoplastic cells. One challenge in exploiting genetic alterations for this purpose is that the concentration of mutant templates is often low in bodily fluids. Over the last several years, however, technological advances have made it possible to detect such mutations even when they are rare. These advances have facilitated the detection of altered DNA sequences in plasma, stool, Pap smear fluids, sputum, and urine (20, 21, 23-30). There is a continuing need in the art for more sensitive means to detect cancers.

SUMMARY OF THE INVENTION

According to one aspect of the invention a method is provided. The method comprises assaying for tumor DNA in plasma from a Head and Neck Cell Carcinoma (HNSCC) patient; and assaying for tumor DNA in saliva from a HNSCC patient.

According to another aspect of the invention another method is provided. The method comprises assaying for tumor DNA in plasma from a subject; and assaying for tumor DNA in saliva from a subject.

These and other embodiments which will be apparent to those of skill in the art upon reading the specification provide the art with

BRIEF DESCRIPTION OF THE DRAWINGS

FIGS. 4A-4B. Patient demographics. The clinical information, tumor characteristics, and presence of tumor DNA in samples collected from 93 patients enrolled in this study are listed (OC=oral cavity, OP=oropharynx, L=larynx, H=hypopharynx, and NA=not available).

FIG. 5. Primer sequences used in multiplex assay for identification of driver mutations in tumors. Amplicons included commonly mutated gene regions in HNSCC. Forward primers (SEQ ID NO: 5-49) and Reverse primers (SEQ ID NO: 50-94).

DETAILED DESCRIPTION OF THE INVENTION

Figure 1:
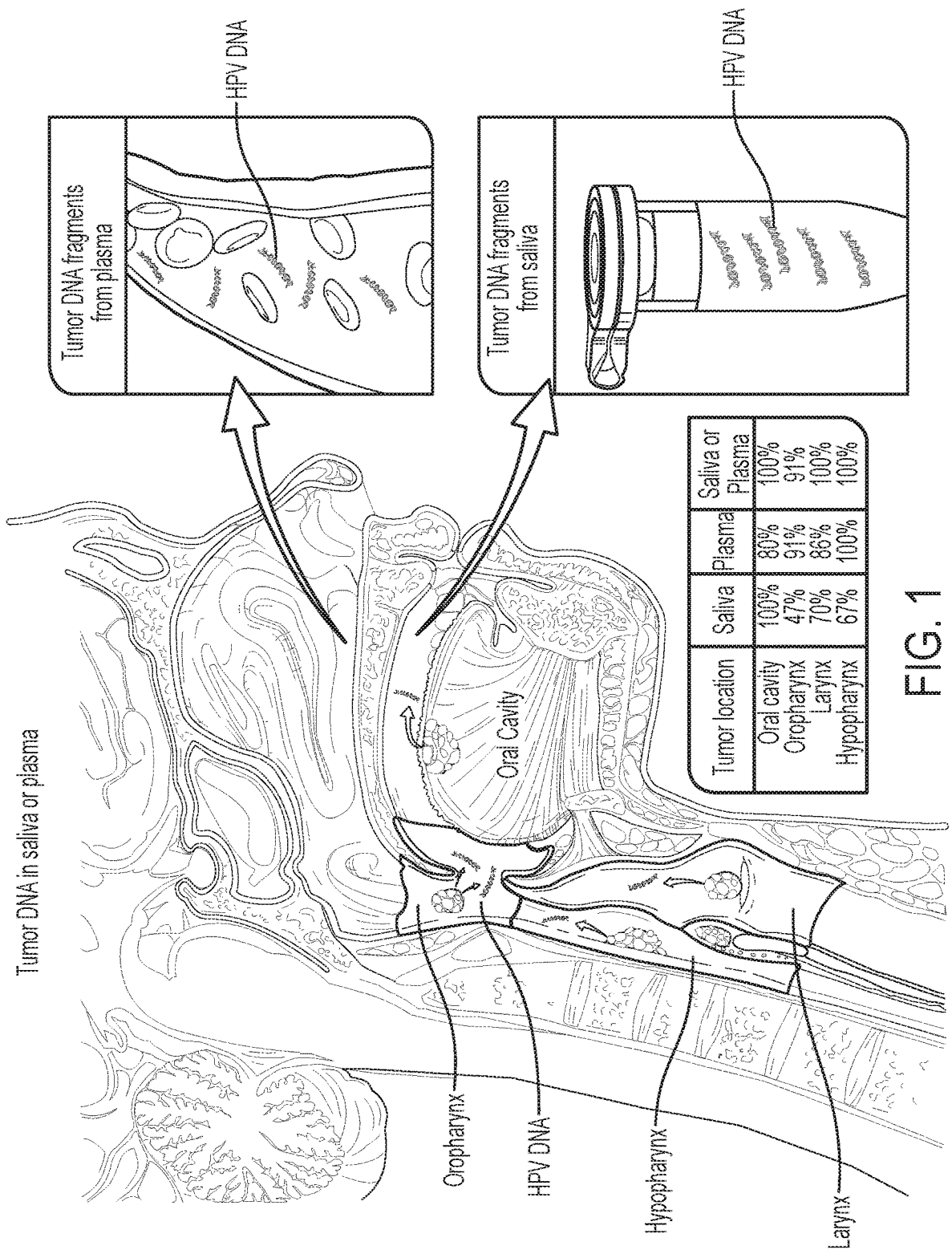
FIG. 1. Schematic drawing showing the shedding of tumor DNA from head and neck cancers into the saliva or plasma. Tumors from various anatomic locations shed DNA fragments containing tumor-specific mutations and HPV DNA into the saliva or the circulation. The detectability of tumor DNA in the saliva varied with anatomic location of the tumor, with the highest sensitivity for oral cavity cancers. The detectability in plasma varied much less in regards to the tumor's anatomic location.

The inventors have developed assays that are useful for detecting, monitoring, and predicting the course of head and neck squamous cell carcinoma (HNSCC). Some of the cancers are associated with HPV infection, and the cancer cells and body fluids contain HPV viral sequences. Some of the cancers are not associated with HPV infection but rather contain somatic mutations that are specific to the cancer. By testing both saliva and plasma of a subject, an extremely high level of sensitivity can be achieved.

HPV sequences which can be used in the assay are any that are found in HNSCC. Typically, the most prevalent are HPV-16 sequences, although HPV-18 sequences are also often found in cancers. Any HPV genetic sequence can be used, including any of genes E1, E2, E3, E4, E5, EC, E7, L1, and L2. Particularly useful genetic sequences are E7 sequences or parts of the E7 sequence.

Somatically mutated genes that frequently occur in HNSCC include but are not limited to TP53, NOTCH1, PI3KCA, CDKN2A, FBXW7, HRAS, and NRAS. In following a single patient one may determine a somatic mutation in a gene in a biopsy or surgical sample. That somatic mutation may be used in subsequent assays in the same or different sample types. If no somatic mutation or HPV infection has been determined for a patient, a panel of frequently-involved-in-HNSCC genes may be used including an HPV-16 sequence, TP53, PIK3CA, NOTCH1, and CDKNA2, for example. Other panels of other frequently mutated genes in HNSCC and HPV sequences may be used as well.

Samples to be assayed for HNSCC related nucleic acid sequences may be from saliva, plasma, or both saliva and plasma. The nucleic acids assayed may be in cells, extracellular, or both. Samples may be collected at multiple time points and assayed in real time, i.e., close to the time of collection, or they may be held and assayed in batches. However, a plasma sample and a saliva sample should preferably be collected at the same time from a subject.

Subjects may have been diagnosed with HNSCC or not prior to performing assays. Subjects may have been subjected to surgery to remove or debulk tumor. Subjects may be at elevated risk for HNSCC due to risky behavior such as exposure to HPV, exposure to tobacco smoke, either primary or secondary, and/or heavy use of alcohol. Subjects may be male or female. Subjects may be related to a patient with HNSCC or not.

Current diagnostic methods for HNSCC make challenging the detection of early disease, assessment of response to treatment, and differentiation between the adverse effects of treatment vs. persistent or recurrent disease. These issues collectively compromise clinical decision-making and impair patient management. Though it is now abundantly clear that all cancers, including HNSCC, are the result of genetic alterations, this knowledge is just beginning to be applied to meet diagnostic challenges such as those described above (10). In this study, we show that tumor-derived DNA can be detected in the saliva of patients with HNSCC. We also show that the evaluation of plasma can complement that of saliva, together allowing detection of tumor-derived DNA in readily obtainable bodily fluids in >90% of the studied patients. Our findings enable clinical tests designed for the earlier detection of HNSCC, either for patients at high risk for the disease or patients previously treated for HNSCC who are at risk for disease recurrence. Moreover, these results enable monitoring the response to treatment.

There were several notable findings in this study. The sensitivity for detection of tumor-derived DNA in the saliva was site-dependent and most efficient for tumors in the oral cavity. Not only was tumor DNA detectable in every one of the 46 patients with cancers of the oral cavity, but the fraction of mutant DNA in the saliva was particularly high (median 0.65%, interquartile range 0.17%-2.2%, mean 3.46%). Moreover, early stage oral cavity cancers were highly detectable; 75% of the patients were oral cavity cancer were at an early stage (Stage I or II), and all were detectable. The high fraction of tumor DNA in the saliva of patients with oral cancers makes anatomical sense and demonstrates the advantage of examining local bodily fluids for optimal sensitivity in this type of assay.

HNSCCs distal to the oral cavity (oropharynx, larynx, and hypopharynx) were still often detectable through the examination of saliva, but the frequency of their detection (47%, 70%, and 67%, respectively) and the fraction of mutant alleles (median 0.015%) were considerably lower than found in the oral cavity (0.65%). Anatomical locations likely explain this difference. Gargling may be used to increase the detectability of tumor DNA in these distal compartments.

One striking aspect of this study is the increased sensitivity demonstrated when both compartments are assayed. This increased sensitivity is possible only because of the exquisite specificity of mutant DNA as biomarker; because no false positives are expected, any number of assays can be combined, increasing sensitivity without compromising specificity. The combination of saliva and plasma allowed detection of 96% of the cancers when both fluids were available, higher than obtained with either saliva or plasma alone.

Our study enables the use of saliva and plasma to reveal the presence of HNSCCs. In each patient, we first evaluated the tumor, then used an alteration (either the presence of HPV or a somatic mutation) to query the saliva or plasma. In a clinical context, a panel of genes should be used to assess each case. Fortunately, technologies are available for finding mutations, even those present at low frequencies (25, 35). Based on the results presented herein, as well as large studies of HNSCC genetics (9, 11, 12), a panel including HPV16 DNA sequences, TP53, PIK3CA, NOTCH1, and CDKA2A would be able to detect >95% of invasive HNSCCs. Another limitation of our study is that the number of early stage cancers beyond the oral cavity was small, in part reflecting the unfortunate fact that most of these cancers are detected only when they are late-stage. Future larger studies should be able to determine how often early stage cancers of the oropharynx, larynx, and hypopharynx can be detected using the approach described here. The fact that at least 70% of the oropharyngeal cancers in the United States are associated with HPV simplifies this task (6, 15).

One important application of our results is in the diagnosis of clinically suspicious lesions. The often complex and highly specialized nature of current HNSCC diagnostic procedures can lead to delays in diagnosis and treatment, negatively impacting prognosis and survival (41-46). These delays could be prevented in many patients through the examination of saliva and plasma for tumor DNA. Such a test could potentially be incorporated into routine examinations to complement current diagnostic modalities and inform clinical decision-making. Another application of our results is in disease monitoring and surveillance. In nine patients with positive pre-treatment saliva and/or plasma, samples were collected at various times after surgery. The fact that no mutations were identified after surgery in the five patients whose tumors did not recur highlights the specificity of the mutation-based assay. It was also encouraging that we identified tumor DNA in the saliva of patients whose tumors were found to recur at the clinical level only months later, indicating that these tests can provide a clinically meaningful lead time. The results presented here indicate that the presence of tumor DNA in either saliva or plasma can be used to help manage patients who appear free of disease after definitive treatment by clinical criteria.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

In this study, we determined whether genetically altered DNA could be detected in the saliva or plasma of HNSCC patients with tumors of various stages and anatomical sites. We chose these two bodily fluids for obvious reasons: plasma has been shown to harbor tumor DNA from many cancers, including HNSCC, though only a few HNSCCs, all of late stage, have been previously examined (23, 31, 32). Tumor DNA that is released from the basal side of HNSCC epithelial cells into the lymphatics or venous system should be detectable in this compartment. On the other hand, DNA that is released primarily on the apical side of HNSCC should be detectable in the saliva (23, 31, 32). The studies described below were performed to test these hypotheses Example 1

Materials and Methods

Study Design

This was a retrospective study with sample collection performed prospectively from 93 HNSCC patients donating saliva, 47 of whom also donating plasma. Data analysis was performed in a blinded fashion and all patient samples were de-identified.

Samples

Figure 6L:
FIGS. 6A-6U. Amounts of tumor-derived DNA in saliva and plasma. The mutation identified in the tumor of each patient is listed, along with the fractions of mutant allele in saliva and plasma. In addition, the numbers of mutant and wild-type reads in patient samples vs. controls are listed for each mutation assayed. For patients with recurrent disease, treatments received and the interval prior to sample collection are listed. Patients in BOLD had both saliva and plasma available (OC=oral cavity, OP=oropharynx, H=hypopharynx, and L=larynx).
Figure 6N:
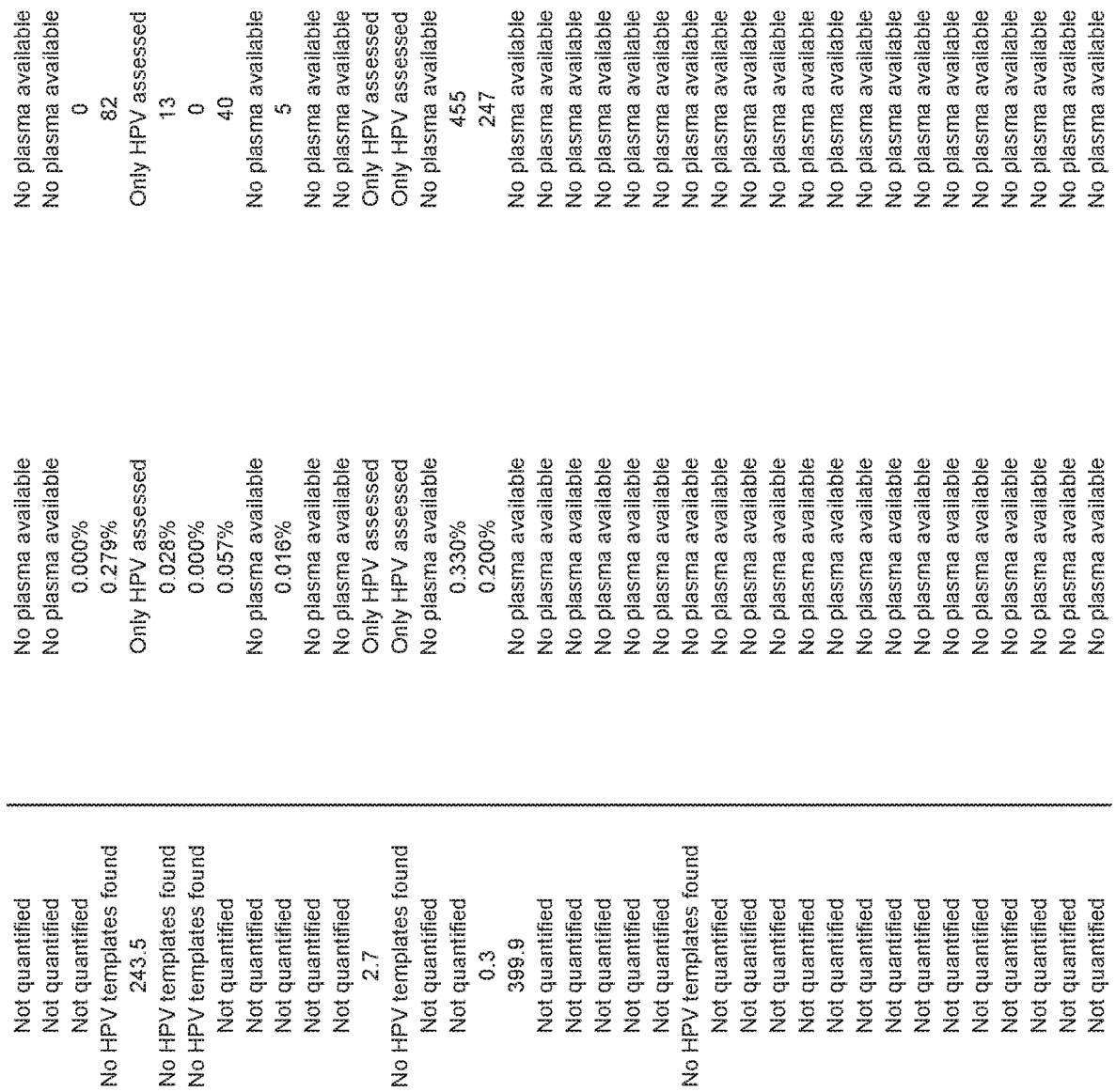
Figure 60:
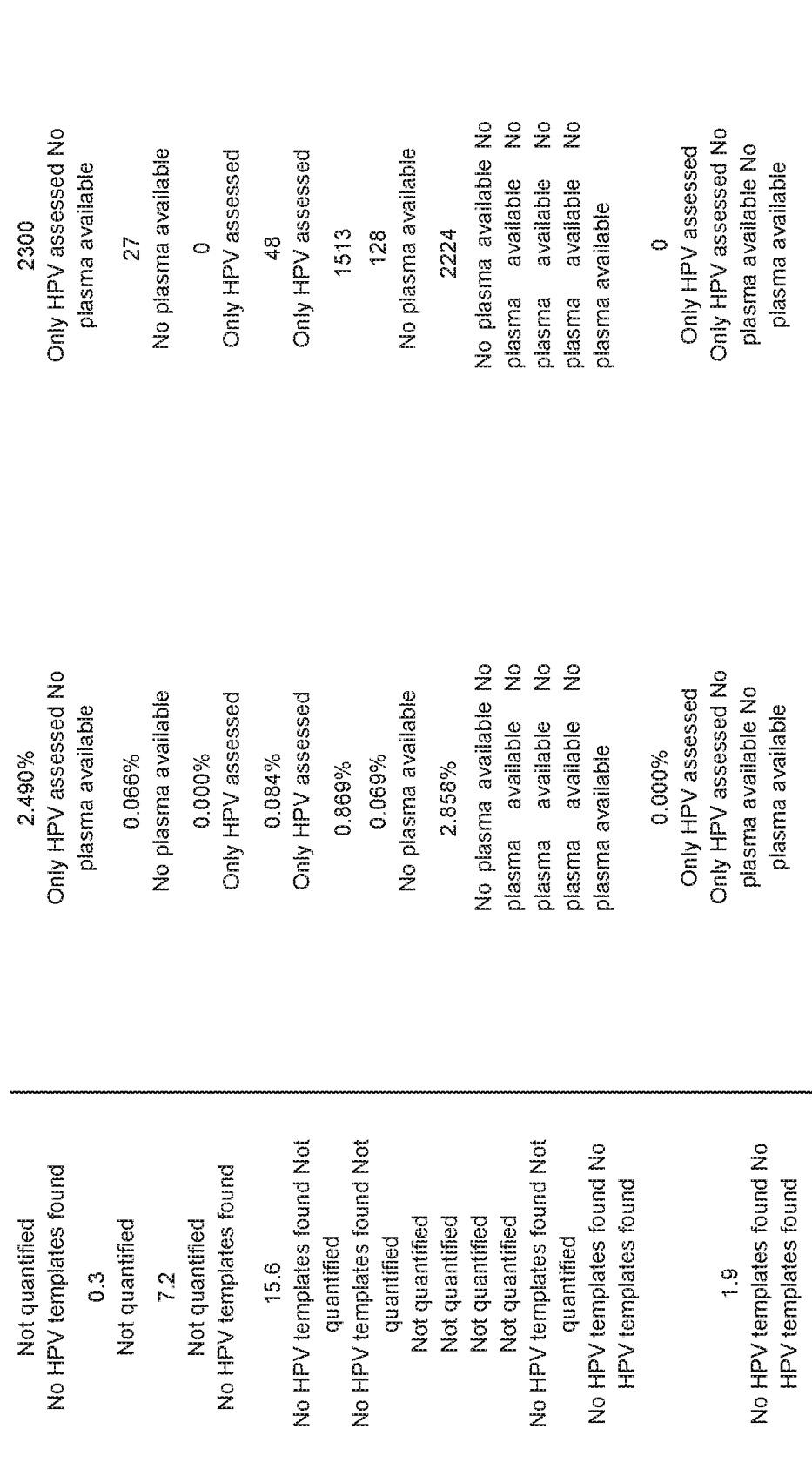
Figure 6R:
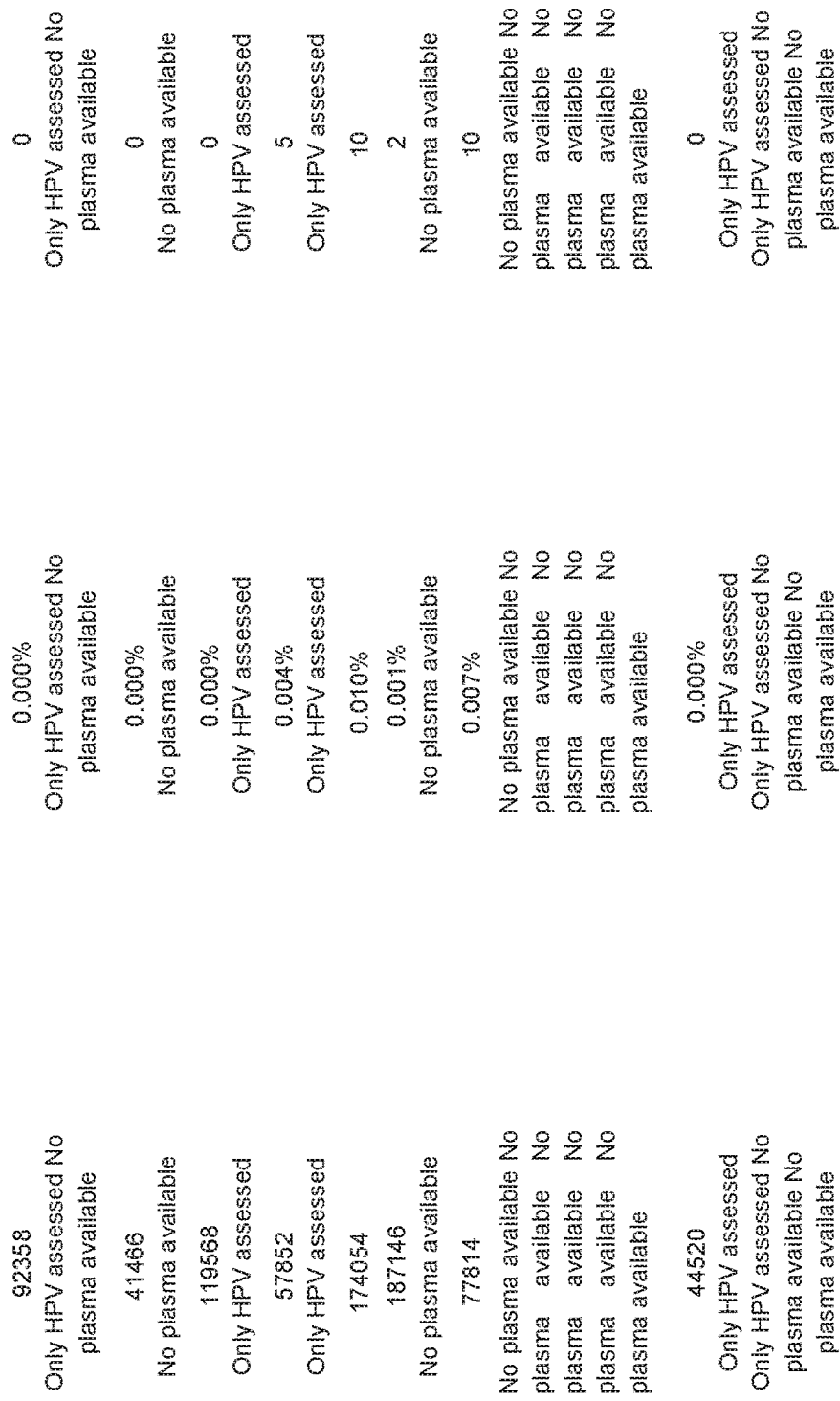

All samples from the 93 patients in this study were collected using Institutional Review Board (IRB) approved protocols at Johns Hopkins University and MD Anderson Medical Center. None of the patients in the current study were included in the previously published study from our groups, in which the genomic landscapes of HNSCC were described (9). Saliva samples were collected before definitive treatment for primary HNSCC (n=71, 76% of 93 patients) and before salvage treatment for recurrent HNSCC (n=22, 24% of 93 patients). In a subset of these patients (n=9), post-treatment saliva was also collected for surveillance. Most patients (95% of the 93) underwent a biopsy of the primary tumor and/or metastatic lymph node, on average 44 days prior to the first sample collection. (FIG. 6.) For the 22 patients with recurrent disease, previous treatment including an iteration of surgery, radiation, and/or chemotherapy was completed an average of 2.9 years before sample collection. (FIG. 6.)

Whole blood was collected from 47 of the 93 patients before treatment. Four to 10 mL of plasma was used for DNA purification, with the average amount of plasma being 6 mL.

Saliva was collected using two different protocols. Under the JHU protocol, patients were asked to swish 15-20 mL of 0.9% sodium chloride in their mouths for 10-15 seconds before spitting into the collection tube. Under the MD Anderson protocol, patients were asked to allow saliva to collect in the floor of the mouth for five minutes without swallowing before spitting into the collection vial. There was no significant difference in the amounts of DNA purified, the fraction of mutant DNA, or the amount of HPV sequences found with the two protocols. Saliva was frozen at −80 C until DNA purification, and the entire volume of saliva, without centrifugation of cells, was used for DNA purification. The amount of saliva used averaged 15 mL (range 10 to 20 mL).

When fresh tumor tissue from a surgical specimen of invasive SCC was available, it was immediately frozen at −80° C. When frozen tissue was not available, formalin-fixed, paraffin-embedded (FFPE) tissues were used for DNA purification. In either case (fresh-frozen or FFPE), tumors were macro-dissected to ensure neoplastic cellularity exceeding 30%. DNA was purified from the white blood cell pellet (normal DNA), saliva, plasma, and tumor using an AllPrep kit (Qiagen, cat #80204).

Tumor Mutational Profiling

A tiered approach was used to identify a somatic mutation within each tumor. Initially, the presence of HPV16 and HPV18 was assessed using the primers specific for the E7 oncogene of these variants (HPV16: TGTGACTC-TACGCTFCGGTTG (SEQ ID NO: 1) and GCCCAT-TAACAGGTCTTCCA (SEQ ID NO: 2); HPV18: GCATGGACCTAAGGCAACAT (SEQ ID NO: 3) and GAAGGTCAACCGGAATTTCAT (SEQ ID NO: 4)). When no HPV was present, multiplex PCR reactions containing primers amplifying regions of interest in TP53, PIK3CA, CDKN2A, FBXW7, HRAS, and NRAS were used to identify driver mutations in the tumors (FIG. 5). If a mutation was not identified in the queried regions, paired-end libraries of DNA from the tumors and white blood cell pellets of each patient were prepared and used for low-coverage whole genome sequencing or exomic sequencing as previously described (47). Massively parallel sequencing was carried out on an Illumina HiSeq instrument, either in the Goldman Sequencing Facility at Johns Hopkins Medical Institutions or at PGDx, Inc. Point mutations were identified as previously described (9, 47, 48), using the following criteria: allele fraction >20%, >5 reads for point mutations, and >1 read for translocations. Genomic rearrangements were identified through an analysis of discordantly mapping paired-end reads. The discordantly mapping paired-end reads were grouped into 1 kb bins when at least 5 distinct tag pairs (with distinct start sites) spanned the same two 1 kb bins, and further annotated based on the approximate breakpoint (34). One selected mutation was confirmed through an independent PCR and sequencing reaction, and then used to query the saliva or plasma.

Mutation Detection in Saliva and Plasma

The same primers used to detect HPV16 in tumor DNA via PCR were used to detect HPV16 sequences in the DNA from saliva or plasma. Each saliva DNA or plasma DNA sample was assessed in at least three independent PCR assays, and all three assays had to be positive for the sample to be counted as positive. As an additional control for specificity, the PCR products were sequenced to ensure that they represented HPV16 sequences. To quantify the amount of HPV16 sequences present in saliva or plasma, we used digital PCR with the same printers (36). Digital PCR was also used to quantify the amount of sequences with translocation using primers spanning the breakpoints, as previously described (49). For evaluation of point mutations in saliva or plasma, we used Safe-SeqS, a PCR-based error-reduction technology for detection of low frequency mutations in reactions each containing up to 3 ng of input DNA (23, 25). High quality sequence reads were selected based on quality scores, which were generated by the sequencing instrument to indicate the probability a base was called in error (50). The template-specific portion of the reads was matched to reference sequences. Reads from a common template molecule were then grouped based on the unique identifier sequences (UIDs) that were incorporated as molecular barcodes. Artifactual mutations introduced during the sample preparation or sequencing steps were reduced by requiring a mutation to be present in >90% of reads in each UID family ("supermutant"). Each PCR assay for each plasma or saliva sample was independently repeated at least three times, with the mutant allele fractions defined as the total number of supermutants divided by the total number of UIDs in all experiments. DNA from normal individuals was used as control, using at least five independent assays per queried mutation. Only saliva or plasma samples in which the mutant allele fractions significantly exceeded their frequencies in control DNA (P-value<0.05) were scored as positive) (details provided in FIG. 6.).

Statistical Analysis

Sensitivity for the detection of tumor-specific mutations in the blood and saliva was calculated by tumor site, stage, and among HPV-associated tumors. Ability to detect tumor DNA in saliva and/or plasma was tested using Fisher's exact tests, and Wilcoxon rank sum tests were used to compare amounts of tumor DNA in saliva vs. plasma (51). For the comparison of mutant fractions in patients vs. control in Safe-SeqS assays, p-values were calculated using a two-sided chi-squared test of equal proportions or Fisher's Exact Test when conditions of the Chi-squared test are not met. The concordance between mutant fractions in saliva and plasma was calculated using Pearson's product-moment correlation coefficient, a standard measure of linear dependence between two variables. All statistical analyses were performed using the R statistical package version 3.1.2.

Example 2

Mutations in Primary Tumors

Ninety-three patients with HNSCC were enrolled in this study. Their average age was 60 and the majority (83%) were male, as is typical of HNSCC patients (FIG. 4). Forty-six, 34, 10, and 3 samples were from the oral cavity, oropharynx, larynx, and hypopharynx, respectively. Twenty patients (22%) had early (Stage I or II) disease and the remaining 73 patients (78%) had advanced (Stage III or IV) disease.

To begin this study, we attempted to identify at least one genetic alteration in each tumor. We first searched for the presence of either HPV16 or HPV18 sequences in tumor DNA. HPV is a well-established etiologic agent for a growing subset of HNSCCs, specifically oropharyngeal SCC (6, 15). With PCR primer pairs specific for the E7 gene of the high-risk HPV types responsible for the overwhelming majority of HPV-associated HNSCC, we identified 30 patients (32%) whose tumors contained HPV16 DNA and no patients with HPV18. The preponderance of HPV16 is not surprising given prior epidemiologic studies of this tumor type (33). In the other 63 patients (all of those without HPV), we searched for somatic mutations in genes or gene regions commonly altered in HNPCC, including TP53, PIK3CA, CDKN2A, FBXW7, HRAS and NRAS, using multiplex PCR and massively parallel sequencing (FIG. 5) (9, 11, 12). This allowed us to identify a driver mutation in 58 of the 63 samples. In the remaining 5 samples, genome-wide sequencing was performed at low coverage with the goal of identifying one driver mutation or translocation as previously described (3-4). Ultimately, we identified and validated one genetic alteration in each of these 63 samples (FIG. 6) The most commonly mutated gene was TP53 (86% of 63 patients). We also searched for mutations in the tumors of 25 of the patients with HPV and found mutations in twelve of those samples (FIG. 6).

Example 3

Mutations in Saliva and Plasma

Important characteristics of screening tests are that samples can be easily collected without discomfort and that the collection process is standardized. To achieve these goals, we used oral rinses, plasma, and commercially available kits to prepare DNA for conventional genotyping purposes. For saliva, we used the entire contents of the collection tube (including cells and cell debris) to prepare DNA. Of the 93 patients who donated saliva for this study prior to their surgery, 47 patients (51%) volunteered to donate plasma at the same time. DNA from plasma was purified as previously described (23). Digital PCR was used to query HPV sequences and translocations (36), whereas point mutations were assessed by Safe SeqS, a PCR-based technology for the detection of low-frequency mutations, as previously described (23, 25, 34-36).

Tumor DNA was identified in 76% (n=93) and 87% (n=47) of the saliva and plasma samples from these patients, respectively (Table 1, FIGS. 4 and 6). In the subset of patients with both plasma and saliva samples, 96% (n=47) of patients had a tumor-alteration identified in at least one bodily fluid. Twenty-one of the 47 patients had HPV-positive tumors. Eighteen of the 21 patients (86%) had detectable HPV DNA in their plasma and/or saliva (Table 1, FIGS. 4 and 6). Because HPV-16 is rarely found in oral specimens of healthy individuals, we analyzed 10 saliva or plasma samples from patients whose tumors were not HPV-positive as controls (37, 38). As expected, no HPV was detected in any of these samples, confirming the specificity of the test. In all 26 patients without HPV-positive tumors, endogenous DNA mutations, mostly in the TP53 gene (92%), were identified in plasma or saliva. (FIG. 6.) Thus, somatic mutations and HPV sequences were both useful as biomarkers for malignancy. The sensitivity of these biomarkers for detecting cancer was greatly improved when both plasma and saliva were examined, compared to testing saliva or plasma alone. There was no significant correlation between the amounts of tumor DNA in saliva vs. plasma in the patients in whom both sample types were available (correlation coefficient of 0.074, p-value=0.74), However, the utility of saliva vs. plasma, and HPV vs. somatic mutations, differed considerably with respect to the site of disease, as noted below.

TABLE 1

Detection of Tumor Derived DNA in Saliva and Plasma. The percentages of patients whose tumors were detectable through the examination of saliva, plasma, or both are shown, grouped by tumor site, stage, and HPV status.

|  | Saliva - % with mutations (95% confidence intervals) (total number studied) | Plasma - % with mutations (95% confidence intervals) (total number studied) | Saliva or plasma - % with mutations (95% confidence intervals) (total number studied)* |
|---|---|---|---|
| Site |  |  |  |
| Oral cavity | 100% (92%-100%) (46) | 80% (52%-96%) (15) | 100% (78%-100%) (15) |
| Oropharynx | 47% (30%-65%) (34) | 91% (71%-99%) (22) | 91% (71%-99%) (22) |
| Larynx | 70% (35%-93%) (10) | 86% (42%-99%) (7) | 100% (59%-100%) (7) |
| Hypopharynx | 67% (9.4%-99%) (3) | 100% (29%-100%) (3) | 100% (29%-100%) (3) |
| Stage |  |  |  |
| Early (I and II) | 100% (83%-100%) (20) | 70% (35%-93%) (10) | 100% (69%-100%) (10) |
| Late (III and IV) | 70% (58%-80%) (73) | 92% (78%-98%) (37) | 95% (82%-99%) (37) |
| HPV |  |  |  |
| Positive | 40% (23%-59%) (30) | 86% (64%-97%) (21) | 86% (64%-97%) (21) |
| Total | 76% (66%-85%) (93) | 87% (74%-95%) (47) | 96% (85%-99%) (47) |

*Includes only patients from whom both saliva and plasma were available.

Example 4

Site

All (100%) of the 46 patients with oral cavity cancers harbored detectable tumor DNA in their saliva (Table 1). The sensitivities of detection in saliva of malignancy at sites not directly sampled by an oral rinse were lower: 47% (n=34), 70% (n=10), and 67% (n=3) of patients with oropharyngeal cancers, laryngeal cancers, and hypopharyngeal cancers had detectable tumor DNA, respectively. The detection rate of tumor DNA in plasma varied less with site, as expected: 80% (n=15), 91% (n=22), 86% (n=7), and 100% (n=3) of tumors of the oral cavity, oropharynx, larynx, and hypopharynx, respectively, had detectable tumor DNA in plasma.

It is well-known that HPV-associated tumors are most often found at specific sites, particularly the oropharynx. Twenty-nine of the 34 (85%) oropharyngeal cancers were HPV-positive. The remaining five oropharyngeal cancers were negative for HPV by PCR, were associated with tobacco use, and harbored TP53 mutations. In striking contrast, all but one of 59 samples from the oral cavity, larynx, and hypopharynx were HPV-negative. The finding that only 1 of the 46 oral cavity cancers tested was HPV-positive is consistent with recent evidence about the low prevalence of HPV-related cancers in the oral cavity (39, 40). For the HPV-associated cancers, which represent 30 (32%) of the total HNSCCs in our study, the presence of HPV DNA in bodily fluids represents a very convenient marker: HPV was detected in 40% (n=30) of saliva samples and 86% (n=21) of available plasma samples with a single primer pair specific for the E7 gene of HPV16 (Table 1).

Collectively, these data indicate that plasma rather than saliva is the optimal fluid for detecting tumor DNA in tumors of the oropharynx, larynx, and hypopharynx. Of the 32 patients with tumors from these sites in which both plasma and saliva were available, mutant DNA was detected in more plasma samples than saliva samples (29 vs. 18, respectively). More importantly, the amount of detectable mutant DNA alleles, expressed as a fraction of the total alleles assessed, was ~10-fold higher in the plasma compared with the saliva of these patients (median 0.146% vs. 0.015%, p=0.005, Wilcoxon rank sum test). (FIG. 6) The higher fraction of alleles considerably simplifies the task of identifying such mutations. This pattern was not observed in the oral cavity: the fraction of patients harboring mutant DNA, as well as the mutant allele fraction, was similar in the saliva and plasma (median 0.65% vs. 0.54%, p=0.14, Wilcoxon rank sum test). (FIG. 6.)

Example 5

Stage

The majority of HNSCC patients have advanced disease (Stage III or IV) at diagnosis (2). Accordingly, only 22% of the 93 patients in our cohort presented with early stage disease. (FIG. 4) Overall, tumor-specific DNA could be detected in the plasma or saliva of 100% (n=20) and 86% (n=73) of patients with early and advanced disease, respectively (p=0.116, Fisher's exact test). Saliva provided a more sensitive predictor of early stage disease than plasma: 100% (15 of 15 oral cavity cancers, 3 of 3 oropharyngeal cancers, and 2 of 2 laryngeal cancers) vs. 70% (5 of 7 oral cavity cancers, 2 of 2 oropharyngeal cancers, and 0 of 1 laryngeal cancers), respectively (p=0.03, Fisher's exact test; Table 1). Contributing to the high sensitivity in saliva was the fact that 75% (15 of 20) of the early-stage cancers in the study were from the oral cavity, which are most readily detectable in saliva and are preferentially treated with surgery, explaining their enrichment in our study. As expected, plasma provided a more sensitive predictor than saliva in patients with advanced stage disease 92% (n=37) vs. 70% (n=73), respectively (p=0.008, Fisher's exact test; Table 1). When segregated by nodal status, tumor-specific DNA could be detected in the plasma or saliva of 83% (n=59) and 100% (n=34) of patients with or without nodal metastasis, respectively. When both saliva and plasma were available, there was little difference between the detectability of cancers with respect to stage of disease (Table 1). An important caveat is that only five patients with early stage disease of non-oral cavity sites were available; though tumor DNA was detectable in all of these patients (all had detectable tumor DNA in saliva; two of the three patients with available plasma also had detectable tumor DNA in their plasma), the amount of tumor DNA was considerably lower than that of late-stage patients (median 0.007% vs 0.06%; p=0.03, Wilcoxon rank sum test).

Example 6

HPV

Thirty patients harbored HPV type 16 DNA in their tumors when assessed by PCR and none had HPV-18. Of these thirty tumors, 29 (97%) were thought to be HPV-associated upon clinical presentation on the basis of in situ hybridization with high-risk HPV sequences or immunohistochemistry with antibodies to p16; in one case, the HPV status had not been determined in the clinic. Additionally, there were no patients who were considered to have HPV-associated tumors in the clinic and did not have HPV16 DNA identified in their tumors by PCR. This supports the specificity and sensitivity of our assays. As expected from the literature, all except one of the thirty tumors containing HPV DNA were found in the oropharynx (15, 39). And as expected, plasma from HPV-associated tumors was more informative than saliva; HPV DNA was detectable in the plasma of 86% (n=21) patients but in only 40% (n=30) of the saliva from these patients (Table 1).

Example 7

Surveillance

Figure 2:
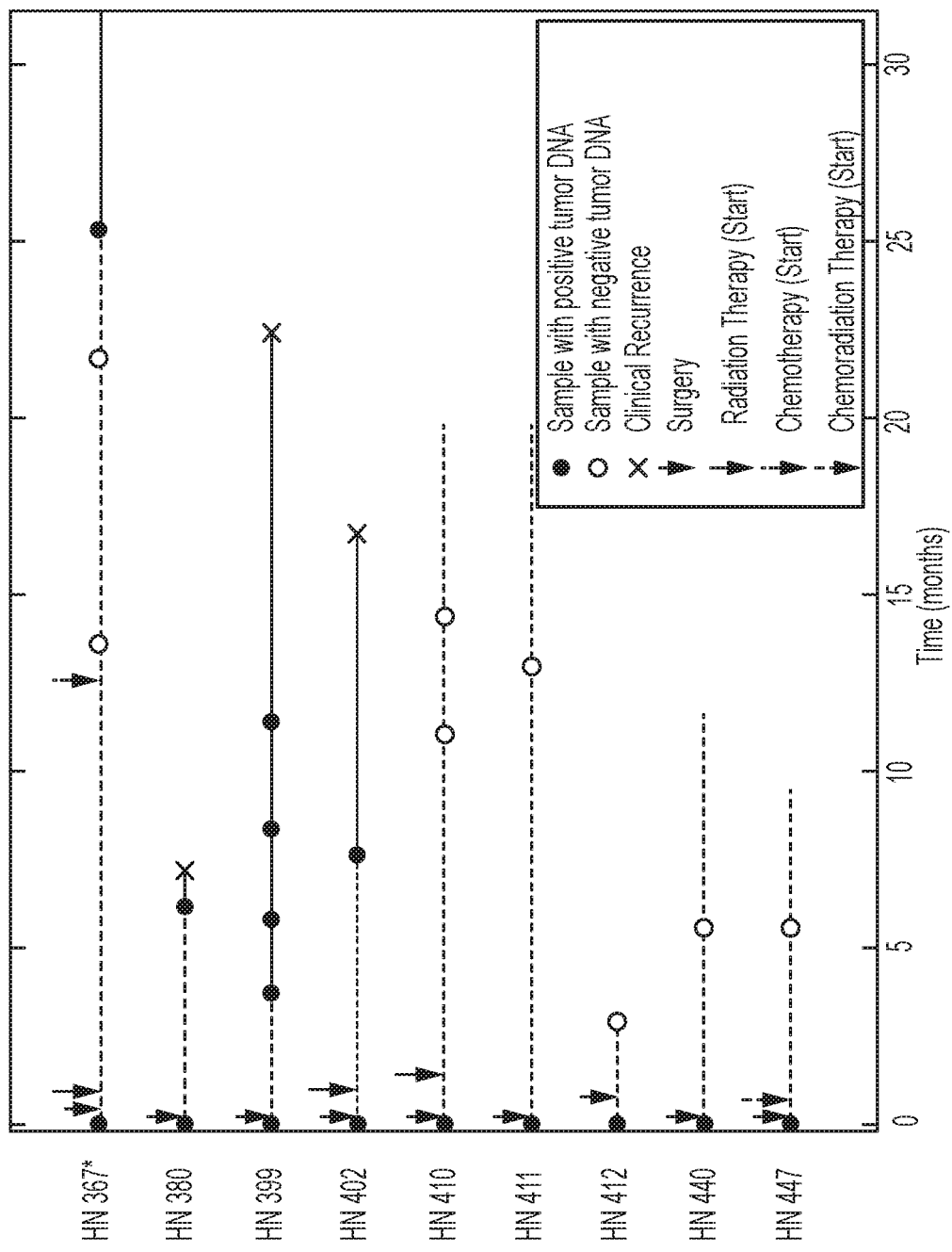
FIG. 2. Tumor DNA is detectable in the saliva of patients before recurrence becomes clinically evident. Nine patients were followed-up for a median of 12 months after surgery. Dashed lines transition to solid lines when tumor DNA was detected after surgery. *Twenty-five months prior to surgery, patient 367 also underwent chemoradiation therapy (not shown).
Figure 3:
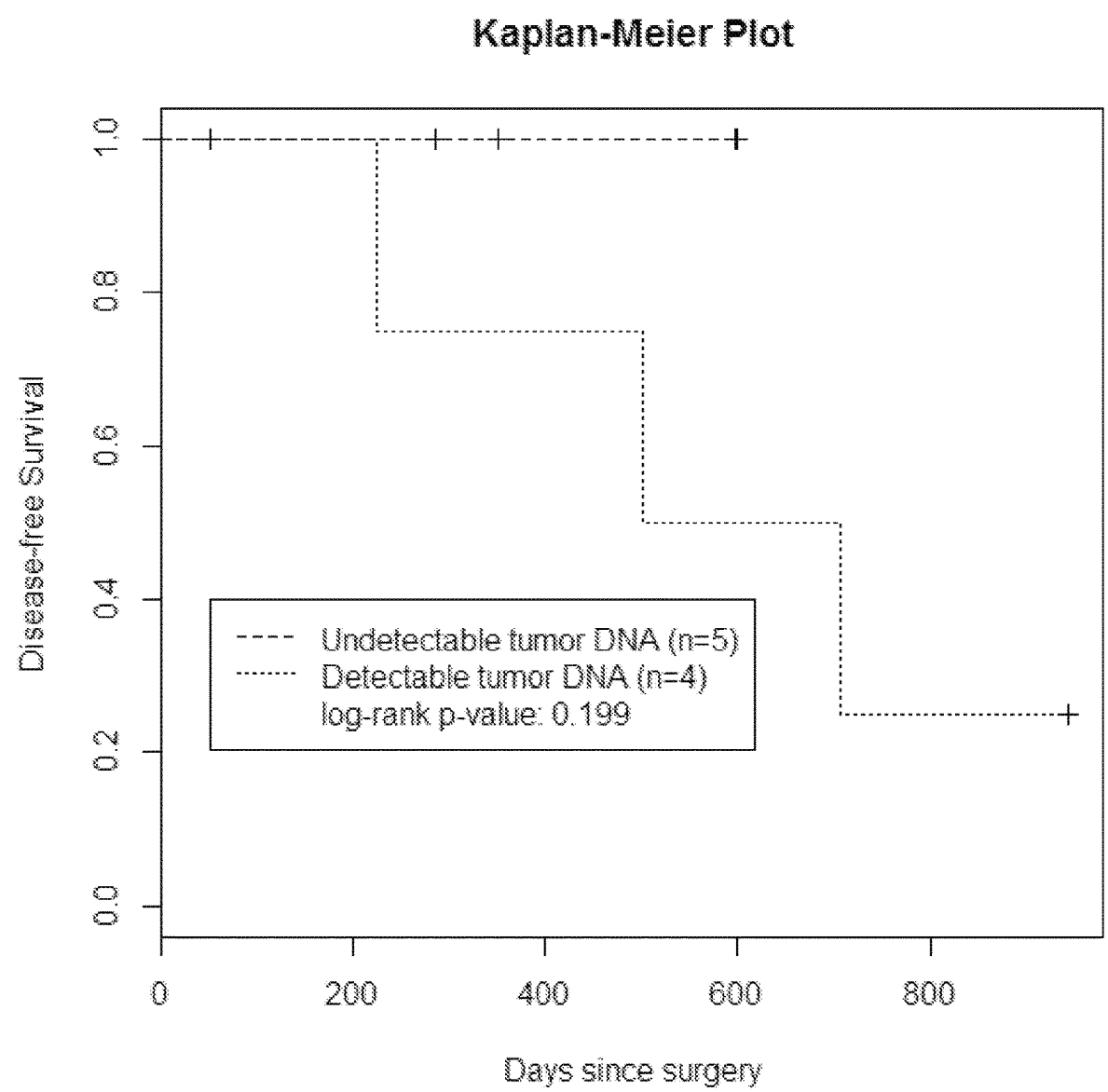
FIG. 3. Patients with undetectable tumor DNA after surgery have better disease-free survival.
Figure 61:
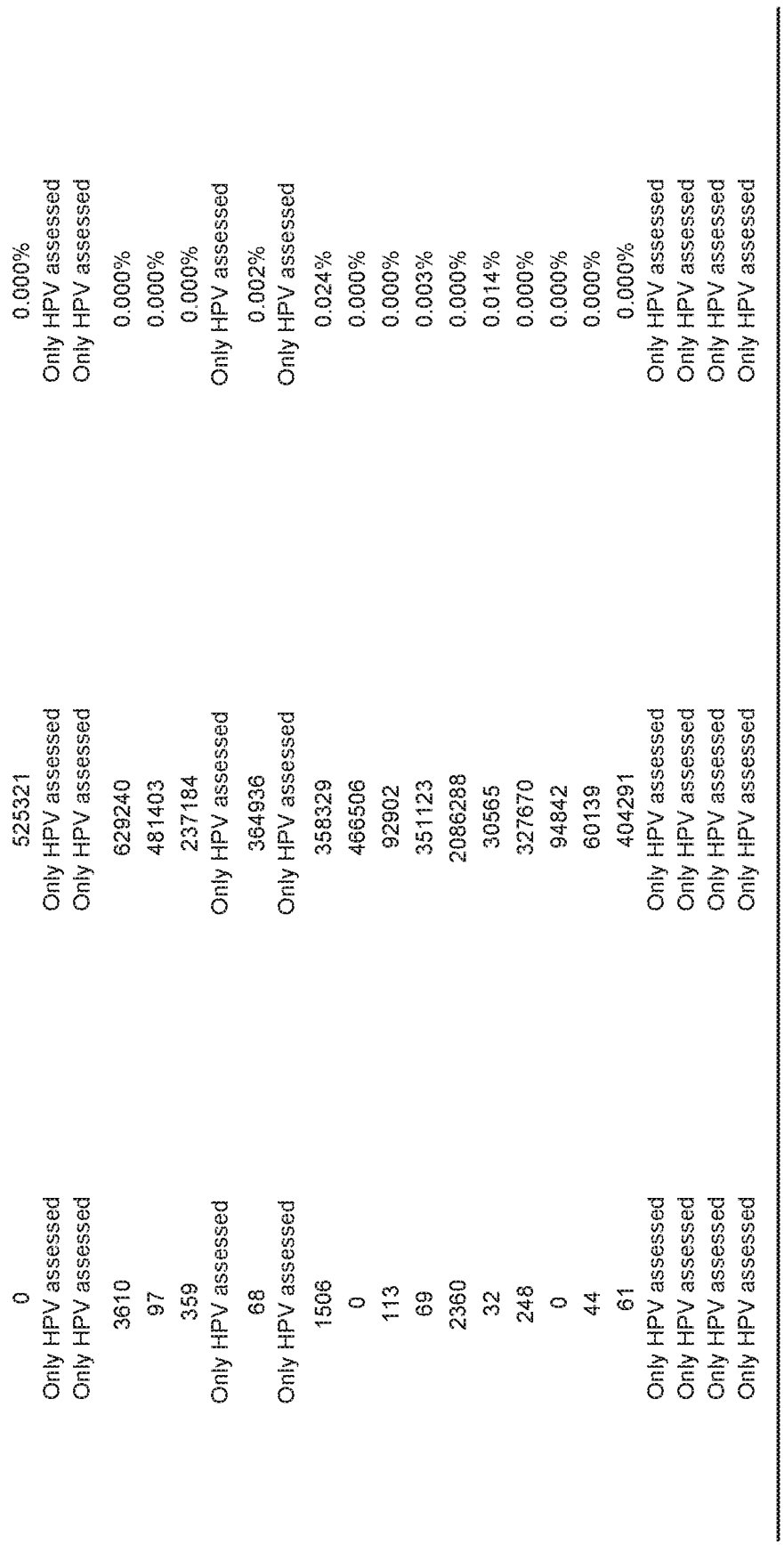

Though not the primary purpose of this study, it was of interest to determine whether tumor DNA could be found in the saliva or plasma of patients after surgical removal of their tumors. "Follow-up" samples were available in nine patients in whom tumor DNA could be identified prior to therapy. Three of these patients were found to have tumor DNA in their saliva or plasma after surgery but before clinical evidence of disease recurrence (FIG. 2). For example, patient HN 399, with cancer of the oral cavity, was found to have tumor DNA in his saliva and plasma 4 months after surgery, whereas the recurrence only became evident clinically 19 months later (23.6 months after surgery). Similarly, tumor DNA was found in the saliva and plasma of patient HN 402, with cancer of the oral cavity, at 8 months after surgery, nine months before the recurrence was clinically evident. Patient HN 380 with cancer of the larynx was found to have tumor DNA in his saliva 7 months after surgery, before any clinical or radiologic evidence of disease recurrence; the patient died of recurrent disease soon thereafter. Tumor DNA was detectable in the saliva of patient HN 367 with cancer of the oropharynx 25 months after surgery; at the time of writing (36 months after surgery), no biopsy-proven disease is yet evident but the clinical course has been complicated with suspicious imaging for locoregional and metastatic disease. No tumor DNA was detectable in the saliva and/or plasma of the other five patients in whom samples were available, all of whom have shown no clinical evidence of recurrence for a median follow-up of 12 months. (FIG. 3)

REFERENCES

The disclosure of each reference cited is expressly incorporated herein.
1. J. Ferlay, H. R. Shin, F. Bray, D. Forman, C. Mathers, D. M. Parkin, Estimates of worldwide burden of cancer in 2008: GLOBOCAN 2008. *International journal of cancer. Journal international du cancer* 127, 2893-2917 (2010).
2. R. L. Siegel, K. D. Miller, A, Jemal, Cancer statistics, 2015. *CA Cancer J Clin*, (2015).
3. E. P. Simard, E. M. Ward, R. Siegel, A. Jemal, Cancers with increasing incidence trends in the United States: 1999 through 2008. *CA Cancer J Clin*, (2012).
4. S. C. Patel, W. R. Carpenter, S. Tyree, M. E. Couch, M. Weissler, T. Hackman, D. N. Hayes, C. Shores, B. S. Chera, Increasing incidence of oral tongue squamous cell carcinoma in young white women, age 18 to 44 years. *Journal of clinical oncology: official journal of the American Society of Clinical Oncology* 29, 1488-1494 (2011).
5. R. Li, D. L. Faden, C. Fakhry, C. Langelier, Y. Jiao, Y. Wang, M. D. Wilkerson, C. S. Pedamallu, M. Old, J. Lang, M. Loyo, S. M. Ahn, M. Tan, Z. Gooi, J. Chan, J. Richmon, L. D. Wood, R. H. Hruban, J. Bishop, W. H. Westra, C. H. Chung, J. Califano, C. G. Gourin, C. Bettegowda, M. Meyerson, N. Papadopoulos, K. W. Kinzler, B. Vogelstein, J. L. DeRisi, W. M. Koch, N. Agrawal, Clinical, genomic, and metagenomic characterization of oral tongue squamous cell carcinoma in patients who do not smoke. *Head & neck*, (2014).
6. A. K. Chaturvedi, E. A. Engels, R. M. Pfeiffer, B. Y. Hernandez, W. Xiao, E. Kim, B. Jiang, M. T. Goodman, M. Sibug-Saber, W. Cozen, L. Liu, C. F. Lynch, N. Wentzensen, R. C. Jordan, S. Altekruse, W. F. Anderson, P. S. Rosenberg, M. L. Gillison, Human papillomavirus and rising oropharyngeal cancer incidence in the United States. *Journal of clinical oncology: official journal of the American Society of Clinical Oncology* 29, 4294-4301 (2011).
7. A. K. Chaturvedi, E. A. Engels, W. F. Anderson, M. L. Gillison, Incidence trends for human papillomavirus-related and-unrelated oral squamous cell carcinomas in the United States. *Journal of clinical oncology: official journal the American Society of Clinical Oncology* 26, 612-619 (2008).
8. C. R. Leemans, B. J. Braakhuis, R. H. Brakenhoff, The molecular biology of head and neck cancer. *Nat Rev Cancer* 11, 9-22 (2011).
9. N. Agrawal, M. J. Frederick, C. R. Pickering, C. Bettegowda, K. Chang, R. J. Li, C. Fakhry, T. X. Xie, J. Mang, J. Wang, N. Zhang, A. K. El-Naggar, S. A. Jasser, J. N. Weinstein, L. Trevino, J. A. Drummond, D. M. Muzny, Y. Wu, L. D. Wood, R. H. Hruban, W. H. Westra, W. M. Koch, J. A. Califano, R. A. Gibbs, D. Sidransky, B. Vogelstein, V. E. Velculescu, N. Papadopoulos, D. A. Wheeler, K. W. Kinzler, J. N. Myers, Exome Sequencing of Head and Neck Squamous Cell Carcinoma Reveals Inactivating Mutations in NOTCH1 *Science*, (2011).
10. B. Vogelstein, N. Papadopoulos, V. E. Velculescu, S. Zhou, L. A. Diaz, Jr., K. W. Kinzler, Cancer genome landscapes. *Science* 339, 1546-1558 (2013).
11. N. Stransky, A, M. Egloff, A. D. Tward, A. D. Kostic, K. Cibulskis, A. Sivachenko, G. V. Kryukov, M. S. Lawrence, C. Sougnez, A. McKenna, E. Shefler, A. H. Ramos, P. Stojanov, S. L. Carter, D. Voet, M. L. Cortes, D. Auclair, M. F. Berger, G. Saksena, C. Guiducci, R. C. Onofrio, M. Parkin, M. Romkes, J. L. Weissfeld, R. R Seethala, L. Wang, C. Rangel-Escareno, J. C. Fernandez-Lopez, A. Hidalgo-Miranda, J. Melendez-Zajgla, W. Winckler, K. Ardlie, S. B. Gabriel, M. Meyerson, E. S. Lander, G. Getz, T. R. Golub, L. A. Garraway, J. R. Grandis, The mutational landscape of head and neck squamous cell carcinoma. *Science* 333, 1157-1160 (2011).

12. Cancer Genome Atlas, Comprehensive genomic characterization of head and neck squamous cell carcinomas. *Nature* 517, 576-582 (2015).

13. N. A. Howlader N, Krapcho M, Garshell J, Miller D, Altekruse S F, Kosary C L, Yu M, J, Tatalovich Z, Mariotto A, Lewis D R, Chen H S, Feuer E J, Cronin K A (eds), SEER Cancer Statistics Review, 1975-2011, National Cancer Institute. Bethesda, Md., based on November 2013 SEER data submission, posted to the SEER web site having the URL seer.cancer.gov/csr/1975_2011/, April 2014.

14. A. K. Chaturvedi, W. F. Anderson, J. Lortet-Tieulent, M. P. Curado, J. Ferlay, S. Franceschi, P. S. Rosenberg, F. Bray, M. L. Gillison, Worldwide trends in incidence rates for oral cavity and oropharyngeal cancers. *Journal of clinical oncology: official journal of the American Society of Clinical Oncology* 31, 4550-4559 (2013).

15. G. D'Souza, A. R. Kreimer, R. Viscidi, M. Pawlita, C. Fakhry, W. M. Koch, W. H. Westra, M. L. Gillison, Case-control study of human papillomavirus and oropharyngeal cancer. *The New England journal of medicine* 356, 1944-1956 (2007).

16. D. G. Pfister, S. Spencer, D. M. Brizel, B. Burtness, P. M. Busse, J. J. Caudell, A. J. Cmelak, A. D. Colevas, F. Dunphy, D. W. Eisele, J. Gilbert, M. L. Gillison, R. I. Haddad, B. H. Haughey, W. L Hicks, Jr., Y. J. Hitchcock, A. Jimeno, M. S. Kies, W. M. Lydiatt, E. Maghami, R. Martins, T. McCaffrey, L. K. Mell, B. B. Mittal, H. A. Pinto, J. A. Ridge, C. P. Rodriguez, S. Samant, D. E. Schuller, J. P. Shah, R S. Weber, G. T. Wolf, F. Worden, S. S. Yom, N. R. McMillian, M. Hughes, Head and neck cancers, Version 2.2014. Clinical practice guidelines in oncology. *J Natl Compr Canc Netw* 12, 1454-1487 (2014).

17. C. G. Gourin, D. J. Terris, Carcinoma of the hypopharynx. *Surg Oncol Clin N Am* 13, 81-98 (2004).

18. P. Kuo, M. M. Chen, R. H. Decker, W. G. Yarbrough, B. L. Judson, Hypopharyngeal cancer incidence, treatment, and survival: temporal trends in the United States. *The Laryngoscope* 124, 2064-2069 (2014).

19. D. Sidransky, Nucleic acid-based methods for the detection of cancer. *Science* 278, 1054-1059 (1997).

20. D. Sidransky, A. Von Eschenbach, Y. C. Tsai, P. Jones, I. Summerhayes, F. Marshall, M. Paul, P. Green, S. R. Hamilton, P. Frost, et al., Identification of p53 gene mutations in bladder cancers and urine samples. *Science* 252, 706-709 (1991).

21. D. Sidransky, T. Tokino, S. R. Hamilton, K. W. Kinzler, B. Levin, P. Frost, B. Vogelstein, Identification of ras oncogene mutations in the stool of patients with curable colorectal tumors. *Science* 256, 102-105 (1992).

22. J. O. Boyle, L. Mao, J. A. Brennan, W. M. Koch, D. W. Eisele, J. R. Saunders, D. Sidransky, Gene mutations in saliva as molecular markers for head and neck squamous cell carcinomas. *American journal of surgery* 168, 429-432 (1994).

23. C. Bettegowda, M. Sausen, R. J. Leary, I. Kinde, Y. Wang, N. Agrawal, B. R. Bartlett, H. Wang, B. Luber, R. M. Alani, E. S. Antonarakis, N. S. Azad, A. Bardelli, H. Brem, J. L. Cameron, C. C. Lee, L. A. Fecher, G. L. Gallia, P. Gibbs, D. Le, R. L. Giuntoli, M. Goggins, M. D. Hogarty, M. Holdhoff, S. M. Hong, Y. Jiao, H. H. Juhl, J. J. Kim, G. Siravegna, D. A. Laheru, C. Lauricella, M. Lim, E. J. Lipson, S. K. Marie, G. J. Netto, K. S. Oliner, A. Olivi, L. Olsson, G. J. Riggins, A. Sartore-Bianchi, K. Schmidt, M. Shih 1, S. M. Oba-Shinjo, S. Siena, D. Theodorescu, J. Tie, T. T. Harkins, S. Veronese, T. L. Wang, J. D. Weingart, C. L. Wolfgang, L. D. Wood, D. Xing, R. H. Hruban, J. Wu, P. J. Allen, C. M. Schmidt, M. A. Choti, V. E. Velculescu, K. W. Kinzler, B. Vogelstein, N. Papadopoulos, L. A. Diaz, Jr., Detection of circulating tumor DNA in early- and late-stage human malignancies. *Science translational medicine* 6, 224ra224 (2014).

24. F. Diehl, K. Schmidt, K. H. Durkee, K. J. Moore, S. N. Goodman, A. P. Shuber, K. W. Kinzler, B. Vogelstein, Analysis of mutations in DNA isolated from plasma and stool of colorectal cancer patients. *Gastroenterology* 135, 489-498 (2008).

25. I. Kinde, C. Bettegowda, Y. Wang, J. Wu, N. Agrawal, M. Shih Ie, R. Kurman, F. Dao, D. A. Levine, R. Giuntoli, R. Roden, J. R. Eshleman, J. P. Carvalho, S. K. Marie, N. Papadopoulos, K. W. Kinzler, B. Vogelstein, L. A. Diaz, Jr., Evaluation of DNA from the Papanicolaou test to detect ovarian and endometrial cancers. *Science translational medicine* 5, 167ra164 (2013).

26. S. J. Dawson, D. W. Tsui, M. Murtaza, H. Biggs, O. M. Rueda, S. F. Chin, M. J. Dunning, D. Gale, T. Forshew, B. Mahler-Araujo, S. Rajan, S. Humphray, J. Becq, D. Halsall, M. Wallis, D. Bentley, C. Caldas, N. Rosenfeld, Analysis of circulating tumor DNA to monitor metastatic breast cancer. *The New England journal of medicine* 368, 1199-1209 (2013).

27. A. M. Newman, S. V. Bratman, J. To, J. F. Wynne, N. C. Eclov, L. A. Modlin, C. L. Liu, J. W. Neal, H. A. Wakelee, R. E. Merritt, J. B. Shrager, B. W. Loo, Jr., A. A. Alizadeh, M. Diehn, An ultrasensitive method for quantitating circulating tumor DNA with broad patient coverage. *Nat Med* 20, 548-554 (2014).

28. J. A. Martignetti, O. Camacho-Vanegas, N. Priedigkeit, C. Camacho, E. Pereira, L. Lin, L. Garnar-Wortzel, D. Miller, B. Losic, H. Shah, J. Liao, J. Ma, P. Lahiri, M. Chee, E. Schadt, P. Dottino, Personalized ovarian cancer disease surveillance and detection of candidate therapeutic drug target in circulating tumor DNA. *Neoplasia* (New York, N.Y.) 16, 97-103 (2014).

29. B. Ralla, C. Stephan, S. Meller, D. Dietrich, G. Kristiansen, K. Jung, Nucleic acid-based biomarkers in body fluids of patients with urologic malignancies. *Crit Rev Clin Lab Sci* 51, 200-231 (2014).

30. A. J. Hubers, C. F. Prinsen, G. Sozzi, B. I. Witte, E. Thunnissen, Molecular sputum analysis for the diagnosis of lung cancer. *British journal of cancer* 109, 530-537 (2013).

31. H. Kang, A. Kiess, C. H. Chung, Emerging biomarkers in head and neck cancer in the era of genomics. *Nat Rev Clin Oncol* 12, 11-26 (2015).

32. S. M. Ahn, J. Y. Chan, Z. Zhang, H. Wang, Z. Khan, J. A. Bishop, W. Westra, W. M. Koch. J. A. Califano, Saliva and plasma quantitative polymerase chain reaction-based detection and surveillance of human papillomavirus-related head and neck cancer, *JAMA Otolaryngol Head Neck Surg* 140, 846-854 (2014).

33. A. R. Kreimer, G. M. Clifford, P. Boyle, S. Franceschi, Human papillomavirus types in head and neck squamous cell carcinomas worldwide: a systematic review. *Cancer epidemiology, biomarkers & prevention: a publication of the American Association for Cancer Research, cosponsored by the American Society of Preventive Oncology* 14, 467-475 (2005).

34. M. Sausen, R. J. Leary, S. Jones, J. Wu, C. P. Reynolds, X. Liu, A. Blackford, G. Parmigiani, L. A. Diaz, Jr., N. Papadopoulos, B. Vogelstein, K. W. Kinzler, V. E. Velculescu, M. D. Hogarty, Integrated genomic analyses identify ARID1A and ARID1B alterations in the childhood cancer neuroblastoma. *Nature genetics* 45, 12-17 (2013).

35. I. Kinde, I Wu, N. Papadopoulos, K. W. Kinzler, B. Vogelstein, Detection and quantification of rare mutations with massively parallel sequencing. *Proceedings of the National Academy of Sciences of the United States of America* 108, 9530-9535 (2012); and U.S. application Ser. No. 14/111,715 (U.S. Pub. No. US-2014-0227705-A1).

36. B. Vogelstein, K. W. Kinzler, Digital PCR. *Proceedings of the National Academy of Sciences of the United States of America* 96, 9236-9241 (1999).

37. A. R. Kreimer, R. K. Bhatia, A, L. Messeguer, P. Gonzalez, R. Herrero, A. R. Giuliano, Oral human papillomavirus in healthy individuals: a systematic review of the literature. *Sexually transmitted diseases* 37, 386-391 (2010).

38. M. L. Gillison, T. Broutian, R. K. Pickard, Z. Y. Tong, W. Xiao, L. Kahle, B. I. Graubard, A. K. Chaturvedi, Prevalence of oral HPV infection in the United States, 2009-2010. *Jama* 307, 693-703 (2012).

39. T. Isayeva, Y. Li, D. Maswahu, M. Brandwein-Gensler, Human papillomavirus in non-oropharyngeal head and neck cancers: a systematic literature review. *Head and neck pathology* 6 Suppl 1. S104-120 (2012).

40. M. W. Lingen, W. Xiao, A. Schmitt, B. Jiang, R. Pickard, P. Kreinbrink, B. Perez-Ordonez, R. C. Jordan, M. L. Gillison, Low etiologic fraction for high-risk human papillomavirus in oral cavity squamous cell carcinomas. *Oral oncology* 49, 1-8 (2013).

41. L. P. Kowalski, A. L. Carvalho, Influence of time delay and clinical upstaging in the prognosis of head and neck cancer. *Oral oncology* 37, 94-98 (2001).

42. J. Guggenheimer, R. S. Verbin, J. T. Johnson, C. A. Horkowitz, E. N. Myers, Factors delaying the diagnosis of oral and oropharyngeal carcinomas. *Cancer* 64, 932-935 (1989).

43. J. Wildt, T. Bundgaard, S. M. Bentzen, Delay in the diagnosis of oral squamous cell carcinoma. *Clin Otolaryngol Allied Sci* 20, 21-25 (1995).

44. P. Allison, E. Franco, M. Black, J. Feine, The role of professional diagnostic delays in the prognosis of upper aerodigestive tract carcinoma. *Oral oncology* 34, 147-153 (1998).

45. A. L. Carvalho, J. Pintos, N. F. Schlecht, B. V. Oliveira, A. S. Fava, M. P. Curado, L. P. Kowalski, E. L. Franco, Predictive factors for diagnosis of advanced-stage squamous cell carcinoma of the head and neck. *Archives of otolaryngology—head & neck surgery* 128, 313-318 (2002).

46. P. Koivunen, N. Rantala, K. Hyrynkangas, K. Jokinen, O. P. Alho, The impact of patient and professional diagnostic delays on survival in pharyngeal cancer. *Cancer* 92, 2885-2891 (2001).

47. N. Agrawal, Y. Jiao, C. Bettegowda, S. M. Hutfless, Y. Wang, S. David, Y. Cheng, W. S. Twaddell, N. L. Latt, E. J. Shin, L. D. Wang, L. Wang, W. Yang, V. E. Velculescu, B. Vogelstein, N. Papadopoulos, K. W. Kinzler, S. J. Meltzer, Comparative Genomic Analysis of Esophageal Adenocarcinoma and Squamous Cell Carcinoma. *Cancer discovery* 2, 899-905 (2012).

48. C. Bettegowda, N. Agrawal, Y. Jiao, M. Sausen, L. D. Wood, R. H. Hruban, F. J. Rodriguez, D. P. Cahill, R. McLendon, G. Riggins, V. E. Velculescu, S. M Ciba-Shinjo, S. K. Marie, B. Vogelstein, D. Bigner, H. Yan, N. Papadopoulos, K. W. Kinzler, Mutations in CIC and FUBP1 contribute to human oligodendroglioma. *Science* 333, 1453-1455(2011).

49. R. J. Leary, I. Kinde, F. Diehl, K. Schmidt, C. Clouser, C. Duncan, A. Antipova, C. Lee, K. McKernan, F. M. De La Vega, K. W. Kinzler, B. Vogelstein, L. A. Diaz, Jr., V. E. Velculescu, Development of personalized tumor biomarkers using massively parallel sequencing. *Science translational medicine* 2, 20ra14 (2010).

50. B. Ewing, L. Hillier, M. C. Wendl, P. Green, Base-calling of automated sequencer traces using phred. I. Accuracy assessment. *Genome Res* 8, 175-185 (1998).

51. A. Agresti, *Categorical Data Analysis*. (Wiley, John & Sons, Incorporated, New York, ed. 2nd, 2002).

We claim:

1. A method of detecting the presence or absence of Head and Neck Squamous Cell Carcinoma comprising:
   (a) assaying a plasma sample from a subject comprising plasma DNA, wherein said assaying comprises performing PCR amplification and/or sequencing of said plasma DNA to detect the presence or absence of: i) HPV 16 nucleic acid, and ii) at least one mutation in each of TP53, PI3KCA, CDKN2A, FBXW7, HRAS, and NRAS; and
   (b) assaying a saliva sample from said subject comprising saliva DNA, wherein said assaying comprises performing PCR amplification and/or sequencing of said saliva DNA to detect the presence or absence of: i) HPV 16 nucleic acid, and ii) at least one mutation in each of TP53, PI3KCA, CDKN2A, FBXW7, HRAS, and NRAS;
   wherein: the presence of HPV 16 nucleic acid, and/or detection of a mutation in TP53, PI3KCA, CDKN2A, FBXW7, HRAS, or NRAS, in the plasma DNA, and/or the saliva DNA, is indicative of the presence of at least one Head and Neck Squamous Cell Carcinoma (HNSCC) selected from: oral cavity HNSCC, oropharynx HNSCC, larynx HNSCC, or hypopharynx HNSCC.

2. The method of claim 1, wherein said subject has not been diagnosed with HNSCC prior to steps (a) and (b).

3. The method of claim 1, wherein the subject has undergone surgical removal of an HNSCC tumor.

4. The method of claim 1, wherein the HNSCC is in the subject's larynx.

5. The method of claim 1, wherein the said plasma and/or saliva DNA is assayed by said sequencing.

6. The method of claim 1, wherein step (a) and step (b) are performed on samples collected from the subject at the same time.

7. The method of claim 6, wherein step (a) and step (b) are performed on a plurality of samples collected from the subject at a plurality of times.

8. The method of claim 1, wherein said sequencing is employed in (a) and (b) and comprises generating sequencing templates from said plasma DNA and said saliva DNA, and wherein molecular barcodes are incorporated into said sequencing templates prior to said sequencing.

9. The method of claim 1, wherein said sequencing is employed in (a) and (b) and comprises generating sequencing templates from said plasma DNA and said saliva DNA, and wherein adapter oligonucleotides are attached to said sequencing templates prior to said sequencing, thereby forming molecular barcodes in said sequencing templates adjacent to said adapter oligonucleotides.

10. The method of claim 1, wherein the subject is at elevated risk for HNSCC.

11. The method of claim 10, wherein the subject is a tobacco smoker, was a tobacco smoker, or was exposed to second hand tobacco smoke.

12. The method of claim 10, wherein the subject is a heavy user of alcohol.

13. The method of claim 1, wherein the HNSCC comprises early stage HNSCC or late stage HNSCC.

14. The method of claim 13, wherein early stage HNSCC comprises a stage I or stage II cancer.

15. The method of claim 13, wherein late stage HNSCC comprises a stage III or stage IV cancer.

16. The method of claim 1, wherein the HNSCC is an oral cavity cancer.

17. The method of claim 1, wherein the HNSCC is a hypopharynx cancer.

18. The method of claim 1, wherein the presence of the TP53 mutation is detected in the saliva sample and is indicative of the presence of early stage HNSCC.

19. The method of claim 1, wherein the presence of the TP53 mutation is detected in the plasma sample and is indicative of the presence of late stage HNSCC.

\* \* \* \* \*

UNITED STATES PATENT AND TRADEMARK OFFICE
CERTIFICATE OF CORRECTION

PATENT NO. : 11,268,153 B2  Page 1 of 1
APPLICATION NO. : 15/739610
DATED : March 8, 2022
INVENTOR(S) : Bert Vogelstein et al.

It is certified that error appears in the above-identified patent and that said Letters Patent is hereby corrected as shown below:

In the Specification

In Column 1, Line 15, delete "NIH", and insert -- the National Institutes of Health --.

Signed and Sealed this
First Day of April, 2025

Coke Morgan Stewart
*Acting Director of the United States Patent and Trademark Office*

SEQUENCE LISTING

<160> NUMBER OF SEQ ID NOS: 94

<210> SEQ ID NO 1
<211> LENGTH: 21
<212> TYPE: DNA
<213> ORGANISM: Homo sapiens

<400> SEQUENCE: 1
tgtgactcta cgcttcggtt g                                            21

<210> SEQ ID NO 2
<211> LENGTH: 20
<212> TYPE: DNA
<213> ORGANISM: Homo sapiens

<400> SEQUENCE: 2
gcccattaac aggtcttcca                                              20

<210> SEQ ID NO 3
<211> LENGTH: 20
<212> TYPE: DNA
<213> ORGANISM: Homo sapiens

<400> SEQUENCE: 3
gcatggacct aaggcaacat                                              20

<210> SEQ ID NO 4
<211> LENGTH: 21
<212> TYPE: DNA
<213> ORGANISM: Homo sapiens

<400> SEQUENCE: 4
gaaggtcaac cggaatttca t                                              21

<210> SEQ ID NO 5
<211> LENGTH: 21
<212> TYPE: DNA
<213> ORGANISM: Homo sapiens;

<400> SEQUENCE: 5
gaagtcccaa ccatgacaag a                                              21

<210> SEQ ID NO 6
<211> LENGTH: 23
<212> TYPE: DNA
<213> ORGANISM: Homo sapiens;

<400> SEQUENCE: 6
ttgtttttct gtttctccct ctg                                            23

<210> SEQ ID NO 7
<211> LENGTH: 23
<212> TYPE: DNA
<213> ORGANISM: Homo sapiens;

<400> SEQUENCE: 7
ttgagacagg ccagtgttta cat                                            23

<210> SEQ ID NO 8
<211> LENGTH: 20
<212> TYPE: DNA
<213> ORGANISM: Homo sapiens;

<400> SEQUENCE: 8
gatgtggctc gccaattaac                                                20

<210> SEQ ID NO 9
<211> LENGTH: 21
<212> TYPE: DNA
<213> ORGANISM: Homo sapiens;

<400> SEQUENCE: 9 acaccccccag gattcttaca g                                             21

<210> SEQ ID NO 10
<211> LENGTH: 20
<212> TYPE: DNA
<213> ORGANISM: Homo sapiens;

<400> SEQUENCE: 10 cccctccat caacttcttc                                                 20

<210> SEQ ID NO 11
<211> LENGTH: 20
<212> TYPE: DNA
<213> ORGANISM: Homo sapiens;

<400> SEQUENCE: 11
cagacgcatt tccacagcta                                              20

<210> SEQ ID NO 12
<211> LENGTH: 26
<212> TYPE: DNA
<213> ORGANISM: Homo sapiens;

<400> SEQUENCE: 12
agagatgatt gttgaatttt cctttt                                       26

<210> SEQ ID NO 13
<211> LENGTH: 23
<212> TYPE: DNA
<213> ORGANISM: Homo sapiens;

<400> SEQUENCE: 13
gcatgccaat ctcttcataa atc                                          23

<210> SEQ ID NO 14
<211> LENGTH: 23
<212> TYPE: DNA
<213> ORGANISM: Homo sapiens;

<400> SEQUENCE: 14
tttgatgaca ttgcatacat tcg                                          23

<210> SEQ ID NO 15
<211> LENGTH: 25
<212> TYPE: DNA
<213> ORGANISM: Homo sapiens;

<400> SEQUENCE: 15
caatgaatta agggaaaatg acaaa                                        25

<210> SEQ ID NO 16
<211> LENGTH: 20
<212> TYPE: DNA
<213> ORGANISM: Homo sapiens;

<400> SEQUENCE: 16
ggcaggagac cctgtaggag                                              20

<210> SEQ ID NO 17
<211> LENGTH: 20
<212> TYPE: DNA
<213> ORGANISM: Homo sapiens;

<400> SEQUENCE: 17
gatggcaaac acacacagga                                              20

<210> SEQ ID NO 18
<211> LENGTH: 16
<212> TYPE: DNA
<213> ORGANISM: Homo sapiens;

<400> SEQUENCE: 18
ccgagtggcg gagctg                                                  16

<210> SEQ ID NO 19
<211> LENGTH: 25
<212> TYPE: DNA
<213> ORGANISM: Homo sapiens;

<400> SEQUENCE: 19

```
acaaattctc agatcatcag tcctc                                           25

<210> SEQ ID NO 20
<211> LENGTH: 18
<212> TYPE: DNA
<213> ORGANISM: Homo sapiens;

<400> SEQUENCE: 20
gcaggtaccg tgcgacat                                                   18

<210> SEQ ID NO 21
<211> LENGTH: 17
<212> TYPE: DNA
<213> ORGANISM: Homo sapiens;

<400> SEQUENCE: 21
gggtcgggtg agagtgg                                                    17

<210> SEQ ID NO 22
<211> LENGTH: 18
<212> TYPE: DNA
<213> ORGANISM: Homo sapiens;

<400> SEQUENCE: 22
gctcctcagc caggtcca                                                   18

<210> SEQ ID NO 23
<211> LENGTH: 19
<212> TYPE: DNA
<213> ORGANISM: Homo sapiens;

<400> SEQUENCE: 23
cacctcctct acccgaccc                                                  19

<210> SEQ ID NO 24
<211> LENGTH: 20
<212> TYPE: DNA
<213> ORGANISM: Homo sapiens;

<400> SEQUENCE: 24
ggcctccgac cgtaactatt                                                 20

<210> SEQ ID NO 25
<211> LENGTH: 17
<212> TYPE: DNA
<213> ORGANISM: Homo sapiens;

<400> SEQUENCE: 25
ctcccgctgc agaccct                                                    17

<210> SEQ ID NO 26
<211> LENGTH: 21
<212> TYPE: DNA
<213> ORGANISM: Homo sapiens;

<400> SEQUENCE: 26
ctgtaggacc ttcggtgact g                                               21

<210> SEQ ID NO 27
<211> LENGTH: 21
<212> TYPE: DNA
<213> ORGANISM: Homo sapiens;
```

```
<400> SEQUENCE: 27
ccttccaatg gatccactca c                                              21

<210> SEQ ID NO 28
<211> LENGTH: 19
<212> TYPE: DNA
<213> ORGANISM: Homo sapiens;

<400> SEQUENCE: 28 agcccctag cagagacct                                                  19

<210> SEQ ID NO 29
<211> LENGTH: 21
<212> TYPE: DNA
<213> ORGANISM: Homo sapiens;

<400> SEQUENCE: 29
tgactgctct tttcacccat c                                              21

<210> SEQ ID NO 30
<211> LENGTH: 21
<212> TYPE: DNA
<213> ORGANISM: Homo sapiens;

<400> SEQUENCE: 30
gcaatggatg atttgatgct g                                              21

<210> SEQ ID NO 31
<211> LENGTH: 19
<212> TYPE: DNA
<213> ORGANISM: Homo sapiens;

<400> SEQUENCE: 31
agctcccaga atgccagag                                                 19

<210> SEQ ID NO 32
<211> LENGTH: 19
<212> TYPE: DNA
<213> ORGANISM: Homo sapiens;

<400> SEQUENCE: 32
ctgcaccagc agctcctac                                                 19

<210> SEQ ID NO 33
<211> LENGTH: 21
<212> TYPE: DNA
<213> ORGANISM: Homo sapiens;

<400> SEQUENCE: 33
gcattgaagt ctcatggaag c                                              21

<210> SEQ ID NO 34
<211> LENGTH: 22
<212> TYPE: DNA
<213> ORGANISM: Homo sapiens;

<400> SEQUENCE: 34
gccctgactt tcaactctgt ct                                             22

<210> SEQ ID NO 35
<211> LENGTH: 20
<212> TYPE: DNA
<213> ORGANISM: Homo sapiens;
```

<400> SEQUENCE: 35
ctccgtcatg tgctgtgact                                              20

<210> SEQ ID NO 36
<211> LENGTH: 19
<212> TYPE: DNA
<213> ORGANISM: Homo sapiens;

<400> SEQUENCE: 36
gccatggcca tctacaagc                                               19

<210> SEQ ID NO 37
<211> LENGTH: 18
<212> TYPE: DNA
<213> ORGANISM: Homo sapiens;

<400> SEQUENCE: 37
gtccccaggc ctctgatt                                                18

<210> SEQ ID NO 38
<211> LENGTH: 20
<212> TYPE: DNA
<213> ORGANISM: Homo sapiens;

<400> SEQUENCE: 38
gtggaaggaa atttgcgtgt                                              20

<210> SEQ ID NO 39
<211> LENGTH: 20
<212> TYPE: DNA
<213> ORGANISM: Homo sapiens;

<400> SEQUENCE: 39
tgtgatgatg gtgaggatgg                                              20

<210> SEQ ID NO 40
<211> LENGTH: 22
<212> TYPE: DNA
<213> ORGANISM: Homo sapiens;

<400> SEQUENCE: 40
tggctctgac tgtaccacca tc                                           22

<210> SEQ ID NO 41
<211> LENGTH: 21
<212> TYPE: DNA
<213> ORGANISM: Homo sapiens;

<400> SEQUENCE: 41
tgcctcttgc ttctcttttc c                                            21

<210> SEQ ID NO 42
<211> LENGTH: 19
<212> TYPE: DNA
<213> ORGANISM: Homo sapiens;

<400> SEQUENCE: 42
cgtgtttgtg cctgtcctg                                               19

<210> SEQ ID NO 43
<211> LENGTH: 23
<212> TYPE: DNA

<213> ORGANISM: Homo sapiens;

<400> SEQUENCE: 43
ttttatcacc tttccttgcc tct                                           23

<210> SEQ ID NO 44
<211> LENGTH: 22
<212> TYPE: DNA
<213> ORGANISM: Homo sapiens;

<400> SEQUENCE: 44
aagaagaaaa cggcattttg ag                                            22

<210> SEQ ID NO 45
<211> LENGTH: 17
<212> TYPE: DNA
<213> ORGANISM: Homo sapiens;

<400> SEQUENCE: 45
ccctggctcc ttcccag                                                  17

<210> SEQ ID NO 46
<211> LENGTH: 20
<212> TYPE: DNA
<213> ORGANISM: Homo sapiens;

<400> SEQUENCE: 46
gttccgagag ctgaatgagg                                               20

<210> SEQ ID NO 47
<211> LENGTH: 21
<212> TYPE: DNA
<213> ORGANISM: Homo sapiens;

<400> SEQUENCE: 47
agtctgagtc aggcccttct g                                             21

<210> SEQ ID NO 48
<211> LENGTH: 21
<212> TYPE: DNA
<213> ORGANISM: Homo sapiens;

<400> SEQUENCE: 48
atgtcatctc tcctccctgc t                                             21

<210> SEQ ID NO 49
<211> LENGTH: 20
<212> TYPE: DNA
<213> ORGANISM: Homo sapiens;

<400> SEQUENCE: 49
gccacctgaa gtccaaaaag                                               20

<210> SEQ ID NO 50
<211> LENGTH: 20
<212> TYPE: DNA
<213> ORGANISM: Homo sapiens;

<400> SEQUENCE: 50
cggacactca aagtgtggaa                                               20

<210> SEQ ID NO 51
<211> LENGTH: 20

```
<212> TYPE: DNA
<213> ORGANISM: Homo sapiens;

<400> SEQUENCE: 51
ctgcaacatg acccatcaaa                                                 20

<210> SEQ ID NO 52
<211> LENGTH: 20
<212> TYPE: DNA
<213> ORGANISM: Homo sapiens;

<400> SEQUENCE: 52
cagtctctgg atcccacacc                                                 20

<210> SEQ ID NO 53
<211> LENGTH: 20
<212> TYPE: DNA
<213> ORGANISM: Homo sapiens;

<400> SEQUENCE: 53
gattgtcagt gcgcttttcc                                                 20

<210> SEQ ID NO 54
<211> LENGTH: 20
<212> TYPE: DNA
<213> ORGANISM: Homo sapiens;

<400> SEQUENCE: 54
cgcctgtcct catgtattgg                                                 20

<210> SEQ ID NO 55
<211> LENGTH: 20
<212> TYPE: DNA
<213> ORGANISM: Homo sapiens;

<400> SEQUENCE: 55
gaaaaagccg aaggtcacaa                                                 20

<210> SEQ ID NO 56
<211> LENGTH: 22
<212> TYPE: DNA
<213> ORGANISM: Homo sapiens;

<400> SEQUENCE: 56
acattcacgt aggttgcaca aa                                              22

<210> SEQ ID NO 57
<211> LENGTH: 23
<212> TYPE: DNA
<213> ORGANISM: Homo sapiens;

<400> SEQUENCE: 57
agtttatatt tccccatgcc aat                                             23

<210> SEQ ID NO 58
<211> LENGTH: 20
<212> TYPE: DNA
<213> ORGANISM: Homo sapiens;

<400> SEQUENCE: 58
tccaaagcct cttgctcagt                                                 20

<210> SEQ ID NO 59
```

```
<211> LENGTH: 25
<212> TYPE: DNA
<213> ORGANISM: Homo sapiens;

<400> SEQUENCE: 59
gatccaatcc atttttgttg tccag                                    25

<210> SEQ ID NO 60
<211> LENGTH: 25
<212> TYPE: DNA
<213> ORGANISM: Homo sapiens;

<400> SEQUENCE: 60
ctccatttta gcacttacct gtgac                                    25

<210> SEQ ID NO 61
<211> LENGTH: 20
<212> TYPE: DNA
<213> ORGANISM: Homo sapiens;

<400> SEQUENCE: 61
gttctggatc agctggatgg                                          20

<210> SEQ ID NO 62
<211> LENGTH: 20
<212> TYPE: DNA
<213> ORGANISM: Homo sapiens;

<400> SEQUENCE: 62
gtggtcattg atggggagac                                          20

<210> SEQ ID NO 63
<211> LENGTH: 19
<212> TYPE: DNA
<213> ORGANISM: Homo sapiens;

<400> SEQUENCE: 63
caccagcgtg tccaggaag                                           19

<210> SEQ ID NO 64
<211> LENGTH: 16
<212> TYPE: DNA
<213> ORGANISM: Homo sapiens;

<400> SEQUENCE: 64
aggagctggg ccatcg                                              16

<210> SEQ ID NO 65
<211> LENGTH: 18
<212> TYPE: DNA
<213> ORGANISM: Homo sapiens;

<400> SEQUENCE: 65
cttcctggac acgctggt                                            18

<210> SEQ ID NO 66
<211> LENGTH: 21
<212> TYPE: DNA
<213> ORGANISM: Homo sapiens;

<400> SEQUENCE: 66
tggctctgac cattctgttc t                                        21
```

```
<210> SEQ ID NO 67
<211> LENGTH: 17
<212> TYPE: DNA
<213> ORGANISM: Homo sapiens;

<400> SEQUENCE: 67 gacccccgcca ctctcac                                                 17

<210> SEQ ID NO 68
<211> LENGTH: 16
<212> TYPE: DNA
<213> ORGANISM: Homo sapiens;

<400> SEQUENCE: 68
ggggagagca ggcagc                                                   16

<210> SEQ ID NO 69
<211> LENGTH: 17
<212> TYPE: DNA
<213> ORGANISM: Homo sapiens;

<400> SEQUENCE: 69
agccttcggc tgactgg                                                  17

<210> SEQ ID NO 70
<211> LENGTH: 19
<212> TYPE: DNA
<213> ORGANISM: Homo sapiens;

<400> SEQUENCE: 70
gggtcgggta gaggaggtg                                                19

<210> SEQ ID NO 71
<211> LENGTH: 20
<212> TYPE: DNA
<213> ORGANISM: Homo sapiens;

<400> SEQUENCE: 71
tgtgccacac atctttgacc                                               20

<210> SEQ ID NO 72
<211> LENGTH: 18
<212> TYPE: DNA
<213> ORGANISM: Homo sapiens;

<400> SEQUENCE: 72
actgccttcc gggtcact                                                 18

<210> SEQ ID NO 73
<211> LENGTH: 19
<212> TYPE: DNA
<213> ORGANISM: Homo sapiens;

<400> SEQUENCE: 73
cagcccaacc cttgtcctt                                                19

<210> SEQ ID NO 74
<211> LENGTH: 20
<212> TYPE: DNA
<213> ORGANISM: Homo sapiens;

<400> SEQUENCE: 74
tcatctggac ctgggtcttc                                               20
```

```
<210> SEQ ID NO 75
<211> LENGTH: 18
<212> TYPE: DNA
<213> ORGANISM: Homo sapiens;

<400> SEQUENCE: 75
cggtgtagga gctgctgg                                                   18

<210> SEQ ID NO 76
<211> LENGTH: 20
<212> TYPE: DNA
<213> ORGANISM: Homo sapiens;

<400> SEQUENCE: 76
tgggaaggga cagaagatga                                                 20

<210> SEQ ID NO 77
<211> LENGTH: 20
<212> TYPE: DNA
<213> ORGANISM: Homo sapiens;

<400> SEQUENCE: 77
cagaatgcaa gaagcccaga                                                 20

<210> SEQ ID NO 78
<211> LENGTH: 20
<212> TYPE: DNA
<213> ORGANISM: Homo sapiens;

<400> SEQUENCE: 78
cccttcccag aaaacctacc                                                 20

<210> SEQ ID NO 79
<211> LENGTH: 18
<212> TYPE: DNA
<213> ORGANISM: Homo sapiens;

<400> SEQUENCE: 79
gggggtgtgg aatcaacc                                                   18

<210> SEQ ID NO 80
<211> LENGTH: 22
<212> TYPE: DNA
<213> ORGANISM: Homo sapiens;

<400> SEQUENCE: 80
caacaagatg ttttgccaac tg                                              22

<210> SEQ ID NO 81
<211> LENGTH: 19
<212> TYPE: DNA
<213> ORGANISM: Homo sapiens;

<400> SEQUENCE: 81
accagccctg tcgtctctc                                                  19

<210> SEQ ID NO 82
<211> LENGTH: 22
<212> TYPE: DNA
<213> ORGANISM: Homo sapiens;

<400> SEQUENCE: 82
cgaaaagtgt ttctgtcatc ca                                              22
```

<210> SEQ ID NO 83
<211> LENGTH: 20
<212> TYPE: DNA
<213> ORGANISM: Homo sapiens;

<400> SEQUENCE: 83
cttaacccct cctcccagag                                                     20

<210> SEQ ID NO 84
<211> LENGTH: 21
<212> TYPE: DNA
<213> ORGANISM: Homo sapiens;

<400> SEQUENCE: 84
tcatcttggg cctgtgttat c                                                   21

<210> SEQ ID NO 85
<211> LENGTH: 18
<212> TYPE: DNA
<213> ORGANISM: Homo sapiens;

<400> SEQUENCE: 85
gtggcaagtg gctcctga                                                       18

<210> SEQ ID NO 86
<211> LENGTH: 21
<212> TYPE: DNA
<213> ORGANISM: Homo sapiens;

<400> SEQUENCE: 86
gcggagattc tcttcctctg t                                                   21

<210> SEQ ID NO 87
<211> LENGTH: 20
<212> TYPE: DNA
<213> ORGANISM: Homo sapiens;

<400> SEQUENCE: 87
gcttcttgtc ctgcttgctt                                                     20

<210> SEQ ID NO 88
<211> LENGTH: 25
<212> TYPE: DNA
<213> ORGANISM: Homo sapiens;

<400> SEQUENCE: 88
caagacttag tacctgaagg gtgaa                                               25

<210> SEQ ID NO 89
<211> LENGTH: 20
<212> TYPE: DNA
<213> ORGANISM: Homo sapiens;

<400> SEQUENCE: 89
ccagccaaag aagaaaccac                                                     20

<210> SEQ ID NO 90
<211> LENGTH: 20
<212> TYPE: DNA
<213> ORGANISM: Homo sapiens;

<400> SEQUENCE: 90

```
cttctccccc tcctctgttg                                              20

<210> SEQ ID NO 91
<211> LENGTH: 20
<212> TYPE: DNA
<213> ORGANISM: Homo sapiens;

<400> SEQUENCE: 91
taggaaggca ggggagtagg                                              20

<210> SEQ ID NO 92
<211> LENGTH: 21
<212> TYPE: DNA
<213> ORGANISM: Homo sapiens;

<400> SEQUENCE: 92
atgtcatctc tcctccctgc t                                            21

<210> SEQ ID NO 93
<211> LENGTH: 21
<212> TYPE: DNA
<213> ORGANISM: Homo sapiens;

<400> SEQUENCE: 93
agtctgagtc aggcccttct g                                            21

<210> SEQ ID NO 94
<211> LENGTH: 19
<212> TYPE: DNA
<213> ORGANISM: Homo sapiens;

<400> SEQUENCE: 94
gaggctgtca gtggggaac                                               19
```